United States Patent
Takeuchi

(10) Patent No.: US 9,283,311 B2
(45) Date of Patent: Mar. 15, 2016

(54) OXYGENATOR AND EXTRACORPOREAL CIRCUIT

(71) Applicant: TERUMO KABUSHIKI KAISHA, Shibuya-ku (JP)

(72) Inventor: Kazuhiko Takeuchi, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 228 days.

(21) Appl. No.: 14/041,356

(22) Filed: Sep. 30, 2013

(65) Prior Publication Data
US 2014/0030149 A1   Jan. 30, 2014

Related U.S. Application Data

(63) Continuation of application No. PCT/JP2011/077226, filed on Nov. 25, 2011.

(30) Foreign Application Priority Data

Mar. 31, 2011 (JP) .................................. 2011-079882
Mar. 31, 2011 (JP) .................................. 2011-079883

(51) Int. Cl.
A61M 1/16 (2006.01)
A61M 1/36 (2006.01)

(52) U.S. Cl.
CPC ........... *A61M 1/1698* (2013.01); *A61M 1/3666* (2013.01)

(58) Field of Classification Search
CPC  A61M 1/1698; A61M 1/3666; A61M 1/1629
See application file for complete search history.

(56) References Cited

U.S. PATENT DOCUMENTS

| 4,828,543 | A | * | 5/1989 | Weiss et al. .................. 604/6.09 |
| 5,695,717 | A | * | 12/1997 | Polaschegg et al. ............ 422/48 |

(Continued)

FOREIGN PATENT DOCUMENTS

| EP | 1 180 374 A1 | 2/2002 |
| EP | 1 618 906 A1 | 1/2006 |
| EP | 1 810 705 A1 | 7/2007 |
| JP | 2007-14502 A | 1/2007 |
| JP | 2007-190218 A | 8/2007 |

OTHER PUBLICATIONS

International Search Report (PCT/ISA/210) mailed on Feb. 28, 2012, by the Japanese Patent Office as the International Searching Authority for International Application No. PCT/JP2011/077226.
The extended European Search Report issued on Nov. 20, 2014, by the European Patent Office in corresponding European Patent Application No. 11861940.2-1651 (6 pgs).

*Primary Examiner* — Philip R Wiest
*Assistant Examiner* — Benjamin Klein
(74) *Attorney, Agent, or Firm* — Buchanan Ingersoll & Rooney PC

(57) ABSTRACT

An oxygenator includes: a housing; a hollow fiber membrane bundle stored in the housing and having multiple integrated hollow fiber membranes with a gas exchange function; a gas inlet portion and a gas outlet portion provided on the upstream and downstream of gas passages in lumens of the hollow fiber membranes, respectively; a blood inlet portion and a blood outlet portion provided on the upstream and downstream of blood passages outside the hollow fiber membranes, respectively; a first filter member provided on the hollow fiber membrane bundle in contact with a blood outlet portion side surface so as to cover substantially the entire surface and has a function to catch bubbles in blood; and a second filter member that is separated from the first filter member, positioned between the first filter member and the blood outlet portion, and has a function to catch bubbles in blood.

18 Claims, 14 Drawing Sheets

(56) References Cited

U.S. PATENT DOCUMENTS

| | | |
|---|---|---|
| 5,770,149 A | 6/1998 | Raible |
| 2002/0049401 A1 | 4/2002 | Ghelli et al. |
| 2006/0016743 A1 | 1/2006 | Ogihara et al. |
| 2007/0166189 A1 | 7/2007 | Ogihara |
| 2007/0166190 A1* | 7/2007 | Ogihara et al. ............ 422/45 |
| 2010/0269342 A1 | 10/2010 | Carpenter et al. |
| 2011/0268608 A1* | 11/2011 | Reggiani et al. ............ 422/45 |

* cited by examiner

OXYGENATOR AND EXTRACORPOREAL CIRCUIT

CROSS REFERENCES TO RELATED APPLICATIONS

This application is a continuation of International Application No. PCT/JP2011/077226 filed on Nov. 25, 2011, and claims priority to Japanese Application No. 2011-079882 filed on Mar. 31, 2011 and Japanese Application No. 2011-079883 filed on Mar. 31, 2011, the entire content of all three of which is incorporated herein by reference.

TECHNICAL FIELD

The present invention generally relates to oxygenators and extracorporeal circuits.

BACKGROUND DISCUSSION

Known conventional extracorporeal circuits for use in cardiac surgery include a bubble removal device (bubble trap), a centrifugal pump, and an oxygenator arranged in this order from the upstream of a flow path for blood circulation and these components are connected with one another by tubes. An example of this extracorporeal circuit is disclosed in Japanese Application Publication No. 2007-14502. The bubble removal device in this extracorporeal circuit is intended to remove bubbles in blood extracted from a patient's body. The centrifugal pump is a blood bump that performs blood circulation so as to extract blood from a patient's body and return the extracted blood into the patient's body. The oxygenator has a hollow fiber membrane layer in which multiple hollow fiber membranes are integrated to perform gas exchange with blood extracted from a patient's body, that is, oxygenation and decarbonation.

In the thus configured extracorporeal circuit, no blood reservoir is provided to suppress an extracorporeal circulation amount (priming volume) of blood circulating in the circuit from the viewpoint of minimum invasive treatment. However, when a blood reservoir is excluded simply for suppression of extracorporeal blood circulation, it is not possible to remove bubbles from the extracted blood. Thus, the extracorporeal circuit disclosed in Japanese Application Publication No. 2007-14502 is provided with a bubble removal device. If neither a blood reservoir nor a bubble removal device is provided, bubbles in blood flow into the centrifugal pump and thus the centrifugal pump with inflow of the bubbles runs at idle and does not perform the function of blood circulation.

Accordingly, the extracorporeal circuit disclosed in Japanese Application Publication No. 2007-14502 is configured to allow the centrifugal pump to perform the foregoing function in a reliable manner such that a bubble removal device is provided on the upstream of the centrifugal pump to remove bubble from blood by the bubble removal device before flowing the blood into the centrifugal pump.

It is nevertheless desirable to eliminate the bubble removal device to further reduce the extracorporeal circulation amount of blood and pursue minimum invasive treatment.

SUMMARY

According to one aspect, an oxygenator comprises: a housing; a hollow fiber membrane bundle stored in the housing and comprised of multiple integrated hollow fiber membranes to perform gas exchange with blood, with the hollow fiber membranes each possessing a lumen constituting a gas passage for the gas; a gas inlet portion upstream of the gas passages of the hollow fiber membranes; a gas outlet portion downstream of the gas passages of the hollow fiber membranes; a blood inlet portion upstream of blood passages outside the hollow fiber membranes; a blood outlet portion downstream of blood passages outside the hollow fiber membranes; and first and second filter members which both filters out bubbles in the blood. The first filter member is provided on the hollow fiber membrane bundle in contact with a blood outlet portion side surface of the hollow fiber membrane bundle to cover substantially the entire blood outlet portion side surface of the hollow fiber membrane bundle. The second filter member is separated from the first filter member and is positioned between the first filter member and the blood outlet portion.

The oxygenator suppresses the extracorporeal circulation amount of blood extracorporeally circulating to pursue minimum invasive treatment while helping to ensure safety.

The first filter member and the second filter member can each be formed in a sheet shape. And the second filter member is preferably smaller in area than the first filter member.

The housing can be cylinder-shaped, and the first filter member and the second filter member can be arranged to overlap each other in a side view.

The blood outlet portion preferably has a tubular blood outlet port protruding from the housing, and the second filter member is positioned near the end portion of the blood outlet on the housing side.

It is preferred that a gap is formed between the first filter member and the housing, and the housing is provided with a discharge port communicating with the gap and configured to discharge bubbles caught by the second filter member to outside of the housing.

The overall outer shape of the hollow fiber membrane bundle can be substantially cuboidal.

It is also possible for the overall outer shape of the hollow fiber membrane bundle to be substantially cylindrical. The second filter member can be curved in an arc toward the blood outlet portion.

The housing can be cylinder-shaped, having an inner peripheral portion that is a concave portion at which the second filter member is located, and the second filter member is placed at the concave portion while being curved with the same curvature as that of the inner peripheral portion of the housing, and with the shape of the second filter forming a continued circle together with the inner peripheral portion of the housing, as seen from an axial direction of the housing.

It is preferred that a constituent material for the first filter member and a constituent material for the second filter member are the same. Also, the first filter member and the second filter member are preferably each hydrophilic.

The first filter member and the second filter member are preferably each mesh-shaped. And the mesh size of the first filter member and the mesh size of the second filter member are preferably the same. Further, it is preferred that the mesh size of the first filter member and the mesh size of the second filter member are each 80 μm or less.

According to another aspect, an oxygenator comprises: a housing possessing an inner surface; a hollow fiber membrane bundle located in the housing; a gas inlet; a gas outlet; and blood inlet; and a blood outlet. The hollow fiber membrane bundle includes multiple integrated hollow fiber membranes that perform gas exchange with blood. The hollow fiber membranes each possess a lumen constituting a gas passage for the gas, with the hollow fiber membranes being positioned so that blood passage spaces exist between adjacent hollow fiber membranes through which the blood flows.

The hollow fiber membrane bundle possesses a downstream facing outer surface facing downstream relative to a direction of flow of the blood. The gas inlet is upstream of the gas passages in the hollow fiber membranes, and the gas inlet fluidly communicates with the gas passages in the hollow fiber membranes so that gas in the gas inlet flows into the gas passages. The gas outlet is downstream of the gas passages in the hollow fiber membranes, and the gas outlet fluidly communicates with the gas passages in the hollow fiber membranes so that gas in the gas passages flow outside the housing by way of the gas outlet. The blood inlet is upstream of the blood passage spaces, and the blood inlet communicates with the blood passage spaces so that blood in the blood inlet flows into the blood passage spaces. The blood outlet is downstream of the blood passage spaces, and the blood outlet communicates with the blood passage spaces so that blood in the blood passage spaces flows into the blood outlet. The oxygenator also includes first and second filter members. The first filter member filters out bubbles in the blood that has passed through the blood passage spaces. The first filter member possesses an upstream facing outer surface which faces and directly contacts the downstream facing outer surface of the hollow fiber membrane bundle to cover substantially an entirety of the downstream facing outer surface of the hollow fiber membrane bundle. The second filter member is spaced downstream from the first filter member so that a space exists between the first and second filter members. The second filter member filters out bubbles in the blood which has passed through the first filter member, with the second filter member extending across the blood outlet so that the blood passes through the second filter member before flowing completely through the blood outlet.

In accordance with another aspect, an extracorporeal circuit includes: an oxygenator such as disclosed here, a first blood pump upstream of the oxygenator and configured to transfer blood for extracorporeal circulation; and at least one second blood pump downstream of the oxygenator and configured to transfer blood for extracorporeal circulation.

According to a further aspect, an extracorporeal circuit includes: an oxygenator such as disclosed here; and a blood pump that is provided only downstream of the oxygenator so that there is no blood pump upstream of the oxygenator, wherein the downstream blood pump is configured to transfer blood for extracorporeal circulation.

It is preferred that the extracorporeal circuit further includes a sensor that is provided on the upstream of the oxygenator to detect a pressure on the upstream.

The extracorporeal circuit preferably further includes control means for controlling operations of the blood pump and the sensor, wherein the control means controls operations of the blood pump according to information obtained from the sensor.

It is preferable that operations of the blood pump are controlled to decrease the amount of blood flowing into the oxygenator when the pressure detected by the sensor falls below a predetermined threshold.

In the extracorporeal circuit, it is preferred that the blood pump is a centrifugal pump, and operations of the blood pump are controlled to reduce the rotation speed of the centrifugal pump or stop the centrifugal pump.

The extracorporeal circuit can be configured so that when the pressure detected by the sensor exceeds a predetermined threshold, the rotation speed of the centrifugal pump is reduced and then the pressure is detected again by the sensor, and when the detected pressure then exceeds a predetermined threshold, the centrifugal pump is stopped.

The rotation speed of the centrifugal pump is preferably reduced in a continuous or stepwise manner.

It is preferred that the blood pump is a centrifugal pump.

DETAILED DESCRIPTION

Figure 1:
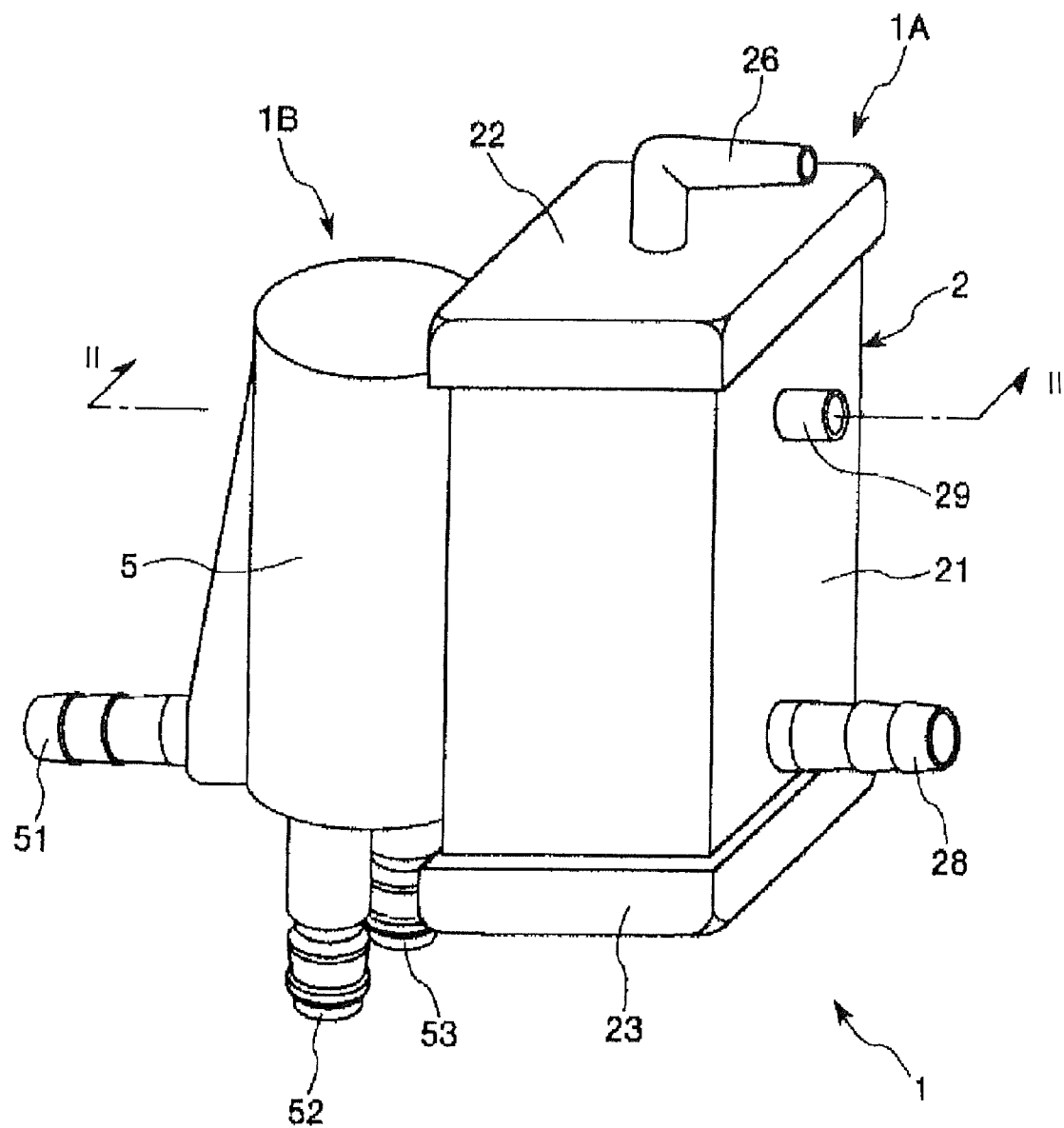
FIG. 1 is a perspective view of a first embodiment of an oxygenator representing an example of the oxygenator disclosed here.
Figure 2:
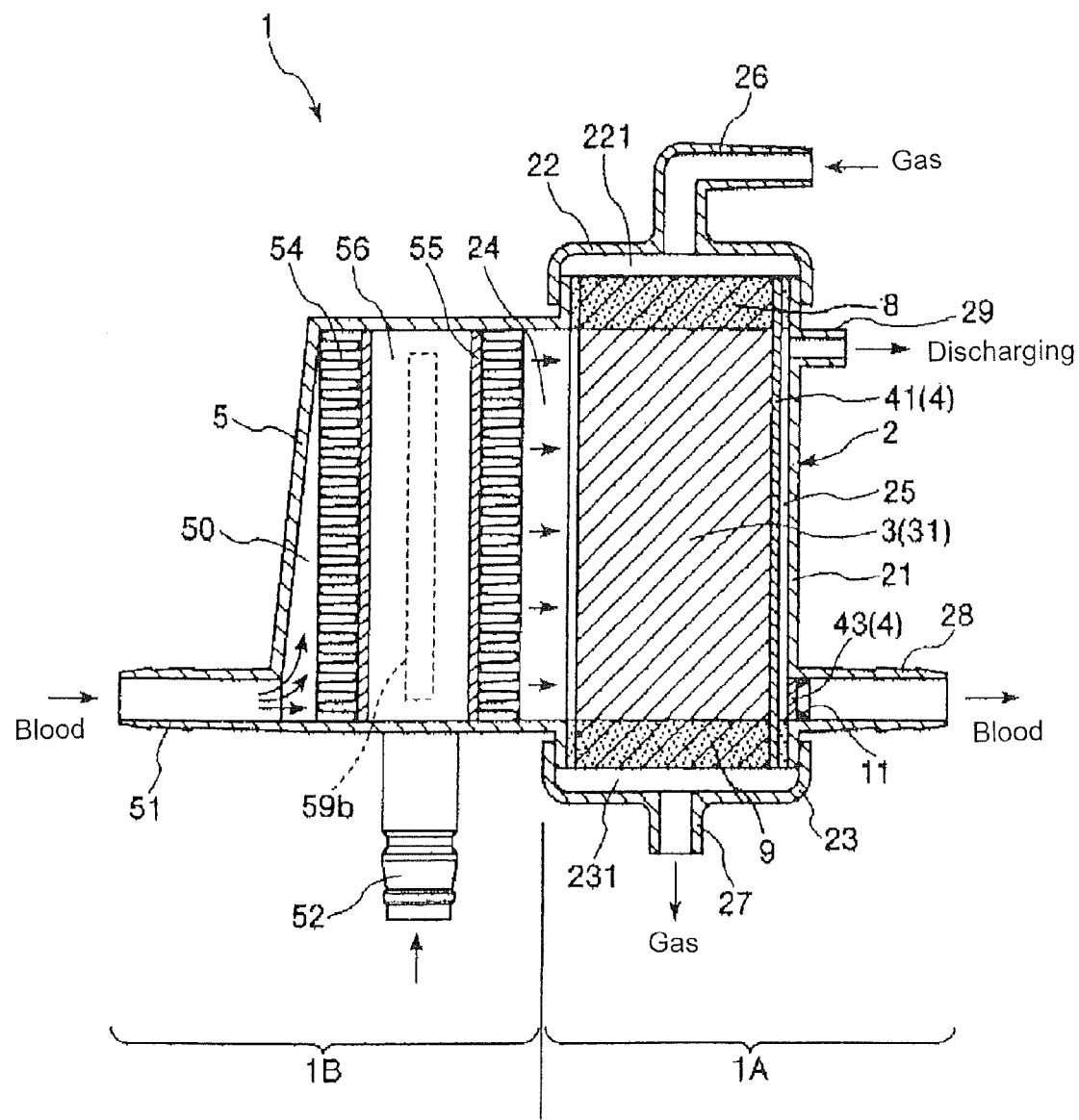
FIG. 2 is a cross-sectional view of the oxygenator taken along the section line II-II in FIG. 1.

Reference is initially made to FIGS. 1-4 which illustrate an embodiment of an oxygenator representing an example of the oxygenator disclosed here. In FIGS. 1 and 2, the upper side is referred to as "upper" or "above," the lower side is referred to as "lower" or "below," the left side is referred to as "blood inlet side" or "upstream," and the right side is referred to as "blood outlet side" or "downstream."

The oxygenator 1 in the illustrated embodiment is a heat exchanger-equipped oxygenator that includes an oxygenating portion 1A configured to perform gas exchange with blood and a heat exchange portion (heat exchanger) 1B configured to perform heat exchange with blood. This oxygenator can be set up in (i.e., be a part of) a blood extracorporeal circuit, for example.

The oxygenator 1 includes a housing 2 located on the oxygenating portion 1A side, and a heat exchanger housing 5 located on the heat exchange portion 1B side. These housings are connected to or integrated with each other. First, the oxygenating portion 1A will be described.

The housing 2 includes a housing body formed in a square cylinder, that is, having a square (quadrate or rectangular) cross section (hereinafter, referred to as "square cylindrical housing body") 21, a dish-shaped first header (upper lid) 22 that closes an upper open end of the square cylindrical housing body 21, and a dish-shaped second header (lower lid) 23 that closes a lower open end of the square cylindrical housing body 21.

The square cylindrical housing body 21, the first header 22, and the second header 23 are each formed by polyolefin such as polyethylene or polypropylene, ester resin (for example, polyester such as polyethylene terephthalate or polybutylene terephthalate), styrene resin (for example, polystyrene, MS resin, or MBS resin), resin materials such as polycarbonate, various kinds of ceramic materials, metal materials, or the like. The first header 22 and the second header 23 are secured to the square cylindrical housing body 21 by adhesion means such as fusing, adhesion using an adhesive, or the like.

The square cylindrical housing body 21 has a circular tube-shaped blood outlet port (blood outlet port) 28 projecting from the lower portion of the housing body 21 on the blood outlet side and a tubular discharge port (discharge port) 29 projecting from the upper portion of the housing body 21 on the blood outlet side. The first header 22 has a tubular gas inlet port 26 projecting from the upper portion of the first header 22. The second header 23 has a tubular gas outlet port 27 projecting from the lower portion of the second header 23. The gas inlet port 26 is bent at substantially a right angle such that the tip end portion of the gas inlet port 26 is parallel to the blood outlet port 28.

The entire shape of the housing 2 is substantially cuboid. Due to the shape of the housing 2, the oxygenator 1 provides the following advantages. The housing 2 is cuboid-shaped and thus can efficiently store hollow fiber membranes 31 in the housing with less dead space to allow efficient gas exchange in the small-sized oxygenator 1. Also, the housing 2 has a flat outer surface, and thus the housing 2 can be fixed to a fixation substrate in a ready and reliable manner. Third, the interior of the housing 2 is defined by flat surfaces, and thus the hollow fiber membranes 31 can be stored in the housing 2 while preventing application of a load on the hollow fiber membranes 31 that might otherwise bend the hollow fiber membranes 31 or the like.

The overall shape of the housing 2 is not necessarily a complete cuboid, but may have chamfered or rounded portions at all or some of corners of the housing. Alternatively, the housing 2 may be partially cut away or provided with a different-shaped portion.

Figure 3:
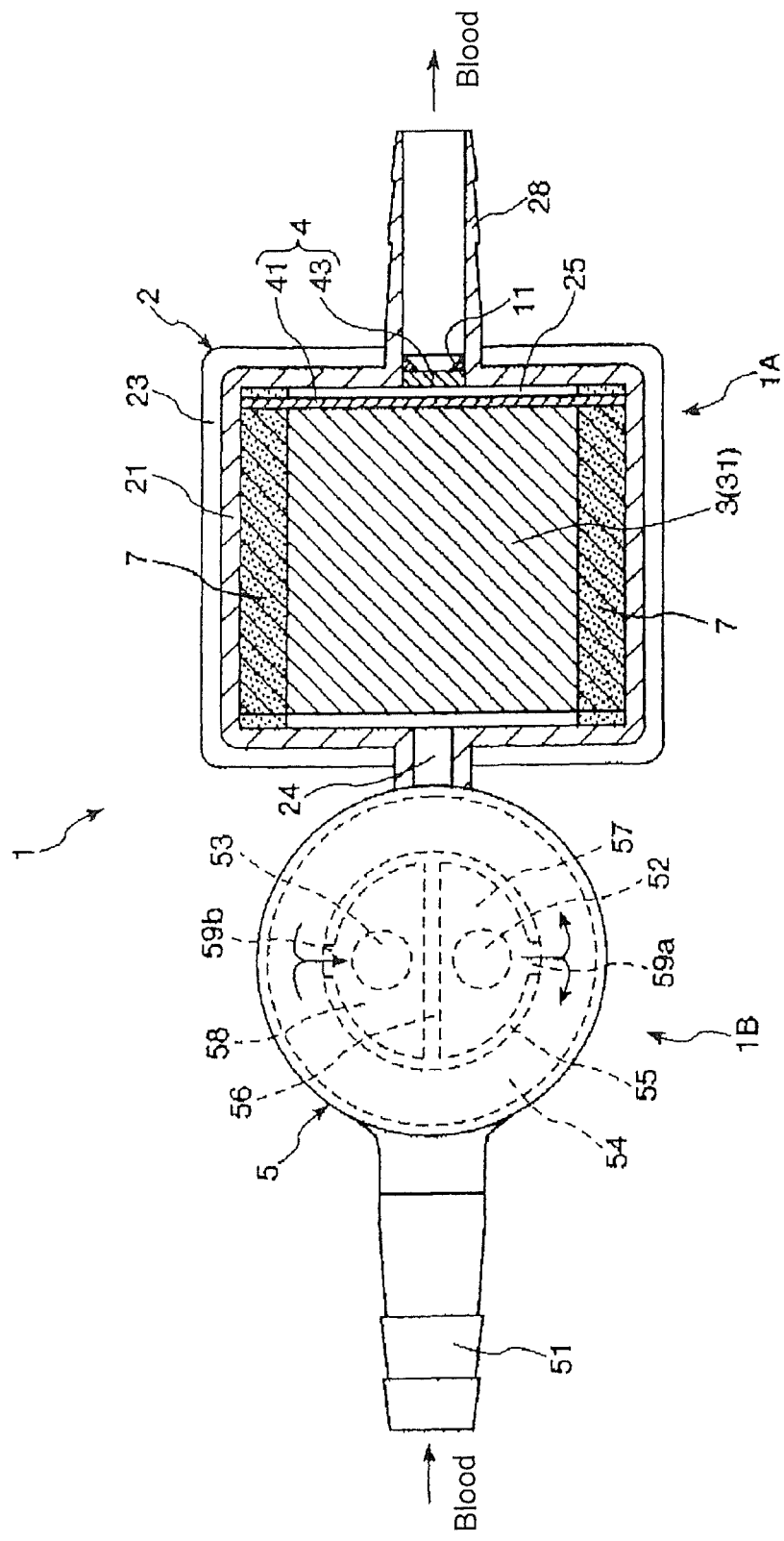
FIG. 3 is a transverse cross-sectional view of an oxygenating portion in the oxygenator illustrated in FIG. 1.
Figure 4:
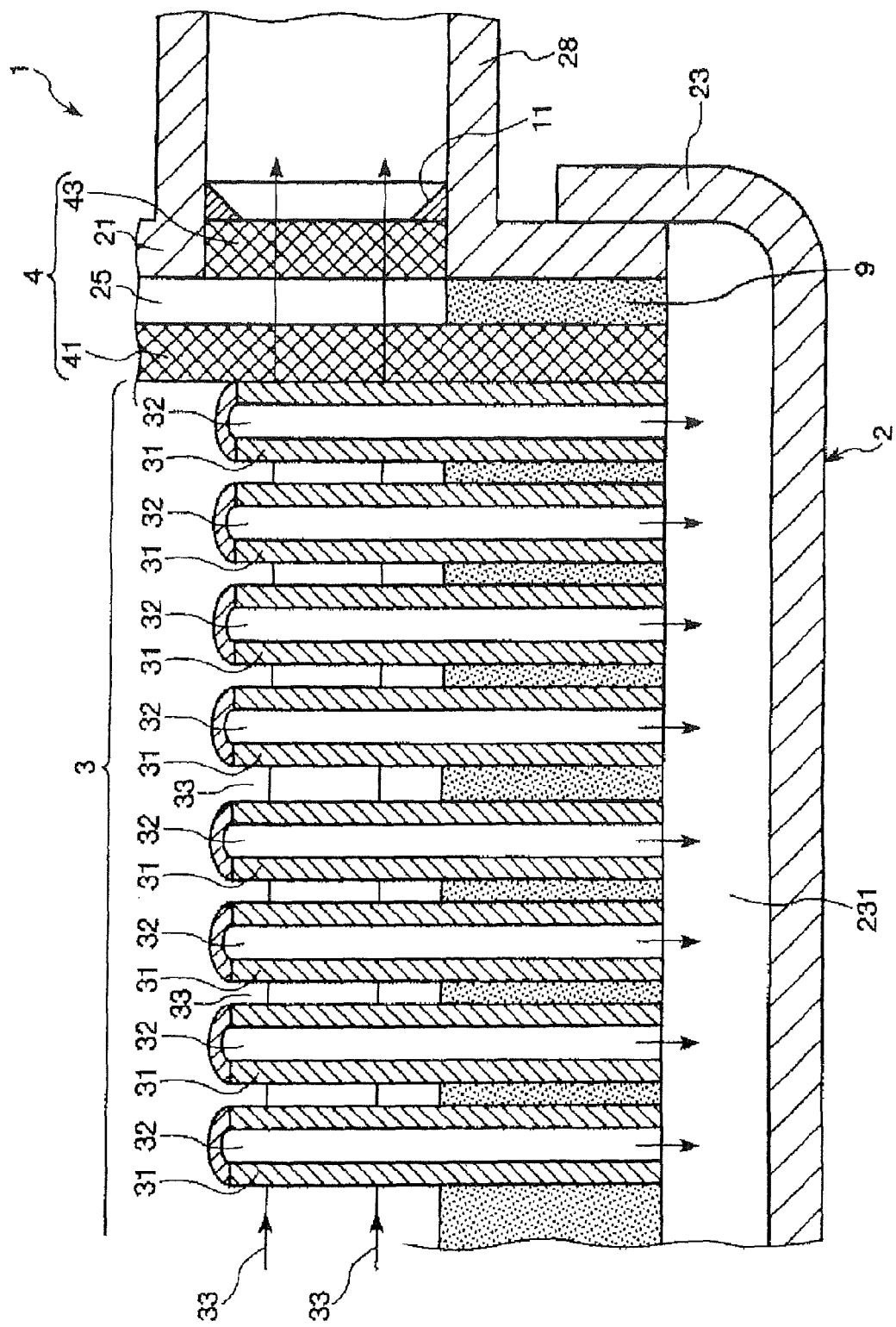
FIG. 4 is an enlarged cross-sectional view of a right lower portion of FIG. 2 (a hollow fiber membrane bundle, a first filter member, and a second filter member).

As illustrated in FIGS. 2 to 4, a hollow fiber membrane bundle 3 is located in the housing 2. The hollow fiber membrane bundle 3 includes multiple integrated hollow fiber membranes 31 with a gas exchange function, and a first filter member 41 and a second filter member 43 as bubble removal means 4 for removing bubbles provided on the blood outlet port 28 (blood outlet portion) side of the hollow fiber membrane bundle 3. The layer 3 and the members 41, 43 are arranged from the blood inlet side in order of the hollow fiber membrane bundle 3, the first filter member 41, and the second filter member 43.

As illustrated in FIG. 4, most of the hollow fiber membranes 31 constituting the hollow fiber membrane bundle 3 are substantially parallel to one another. In this case, the hollow fiber membranes 31 are each oriented with longer sides of the hollow fiber membranes 31 arranged along the up-down direction (vertical direction).

The arrangement pattern, arrangement direction, etc., of the hollow fiber membranes 31 in the hollow fiber membrane bundle 3 are not limited to the ones discussed above. For example, the hollow fiber membranes 31 may be arranged in the horizontal direction, the hollow fiber membranes 31 may have portions at which the hollow fiber membranes 31 obliquely intersect one another (crossing portions), all or some of the hollow fiber membranes 31 may be curved, or all or some of the hollow fiber membranes 31 may be arranged in a corrugated, helical, spiral, or annular form.

The hollow fiber membranes 31 have opposite ends (upper and lower ends) fixed to inner surfaces of the square rectangular housing body 21 by way of partition walls 8 and 9 (see FIG. 2). The partition walls 8 and 9 are formed by a potting material, for example, polyurethane or silicone rubber.

Both ends of the hollow fiber membrane bundle 3 are fixed (secured) by securing portions 7 to inner surfaces of the square rectangular housing body 21 as shown in FIG. 3. The securing portions 7 are formed by the same material (potting material) as that for the partition walls 8 and 9, or another adhesive.

A first chamber 221 is defined by the first header 22 and the partition wall 8. The first chamber 221 is a gas inlet chamber into which gas flows. The hollow fiber membranes 31 have upper end openings open to and communicating with the first chamber 221.

A second chamber 231 is defined by the second header 23 and the partition wall 9. The second chamber 231 is a gas outlet chamber from which gas flows out. The hollow fiber membranes 31 have lower end openings open to and communicating with the second chamber 231 (see FIG. 4).

Lumens of the hollow fiber membranes 31 form gas passages 32 through which gas flows. The gas inlet port 26 and the first chamber 221 constitute a gas inlet portion located on the upstream of the gas passages 32. The gas outlet port 27 and the second chamber 231 constitute a gas outlet portion located on the downstream of the gas passages 32. The gas outlet portion is open to the outside. That is, the gas outlet portion is open to the atmosphere. The gas outlet portion may be connected to wall-mounted suction equipment in an operating room. The wall-mounted suction equipment here refers to a kind of medical gas piping equipment for supplying oxygen, air for therapy, and nitrogen, suctioning, and the like, which is piping equipment for suctioning (deaeration) mounted on a wall of an operating room or the like. The wall-mounted suction equipment allows reliable suction of a gas containing a relatively large amount of carbon dioxide, that is, gas used for gas exchange, via the gas outlet portion.

The hollow fiber membrane bundle 3 is filled in the square cylindrical housing body 21 substantially without space, and thus the overall shape of the hollow fiber membrane bundle 3 is substantially a cuboid. This provides high efficiency of filling the hollow fiber membranes 31 into the similarly shaped square cylindrical housing body 21 (with less dead space), which contributes to smaller size and higher performance of the oxygenating portion 1A.

The hollow fiber membranes 31 are exposed between the partition walls 8 and 9 in the housing 2 to form blood passages 33 outside the hollow fiber membranes 31, that is, in the gaps between the hollow fiber membranes 31 to allow blood to flow from the left side to the right side in FIGS. 2 and 3.

On the upstream of the blood passages 33 (the upstream side of the hollow fiber membrane bundle 3), that is, at a connection portion between the square cylindrical housing body 21 and the heat-exchanger housing 5, a band-shaped or slit-shaped blood inlet-side opening (blood inlet-side space) 24 as a blood inlet portion extending in the vertical direction (substantially parallel to the direction of placement of the hollow fiber membranes 31) is formed. The interior of the housing 2 and the interior of the heat exchanger housing 5 communicate with each other via the blood inlet-side opening 24. The foregoing configuration allows efficient transfer of blood from the heat exchanger 1B to the oxygenating portion 1A.

The length of the blood inlet-side opening 24 (vertical length) is preferably substantially equal to (see FIG. 2) or slightly smaller than effective length of the hollow fiber membranes 31 (from the lower surface of the partition wall 8 to the upper surface of the partition wall 9). This allows efficient transfer of blood from the heat exchanger 1B to the oxygenating portion 1A and efficient gas exchange with blood in the blood passages 33.

At least in a part upstream (blood inlet-side opening 24 side) of the blood passages 33, the direction of flow of blood is substantially orthogonal to the longitudinal sides of the hollow fiber membranes 31. This allows efficient gas exchange with blood flowing through the blood passages 33.

On the downstream of the blood passages 33 (on the downstream-side surface of the hollow fiber membrane bundle 3), a gap exists between the first filter member 41 and the inner surface of the square cylindrical housing body 21. The gap functions as a blood outlet-side opening (blood outlet-side space) 25. The blood outlet-side opening 25 and the blood outlet port 28 communicating with the blood outlet-side opening 25 constitute a blood outlet portion. The blood outlet portion with the blood outlet-side opening 25 provides a space for the blood having flowed through the first filter member 41 to flow toward the blood outlet port 28, thereby allowing smooth discharge of blood.

The hollow fiber membrane bundle 3, the first filter member 41, and the blood passages 33 are present between the blood inlet-side opening 24 and the blood outlet-side opening 25.

As illustrated in FIG. 2, the blood outlet-side opening 25 communicates with the discharge port 29 projecting from the square cylindrical housing body 21.

In the case where a blood pump for suctioning blood from a patient's body is mounted on the downstream of the oxygenator 1 and the rotation speed of the blood pump is excessively higher due to some abnormality, when the blood flows into the oxygenator 1, bubbles in the blood may flow through the first filter member 41. However, the bubbles are caught at the second filter member 43 and then are discharged via the discharge port 29. This discharge makes it possible to remove the bubbles from the oxygenator 1.

Since the bubbles can be caught at the oxygenator 1, the extracorporeal circulation including the oxygenator 1 does not need a bubble removal device that is mounted in conventional extracorporeal circuits. That is, when the oxygenator disclosed here is provided as a part of an extracorporeal circuit, the extracorporeal circuit is devoid of a bubble removal device outside the oxygenator. Accordingly, when no bubble removal device is provided as described above, it is possible to suppress the amount of blood extracorporeally circulating (priming volume).

The hollow fiber membranes 31 uses porous gas exchange films, for example. The porous hollow fiber membranes may have an inner diameter of about 100 to 1000 μm, a wall thickness of about 5 to 200 μm, preferably 10 to 100 μm, a porosity of about 20 to 80%, preferably about 30 to 60%, a pore size of about 0.01 to 5 μm, preferably about 0.01 to 1 μm.

A constituent material for the hollow fiber membranes 31 is a hydrophobic polymer material, for example, polypropylene, polyethylene, polysulfone, polyacrylonitrile, polyterafluoroethylene, or polymethyl pentane. Polyolefin resin is preferred, and polypropylene is more preferred. The constituent material is more preferably configured such that pores are formed in the wall of the material by stretching or solid-liquid phase separation.

Although it is not particularly limited, the length (effective length) of the hollow fiber membranes 31 in the hollow fiber membrane bundle 3 is preferably about 20 to 150 mm, more preferably about 30 to 100 mm.

Also, the thickness of the hollow fiber membrane bundle 3 is not limited to a particular thickness. But the thickness of the hollow fiber membrane bundle 3 (horizontal length in FIG. 2) is preferably about 3 to 100 mm, more preferably about 7 to 50 mm.

Although it is not particularly limited, the width of the hollow fiber membrane bundle 3 (vertical length in FIG. 3) is preferably about 10 to 100 mm, more preferably about 20 to 80 mm.

As described above, the bubble removal means 4 with the function of catching bubbles in blood and removing the same from the blood, is provided on the downstream (blood outlet portion side) of the hollow fiber membrane bundle 3. As illustrated in FIGS. 2 to 4, the bubble removal means 4 has the first filter member 41 and the second filter member 43 located on the downstream of the first filter member 41.

The first filter member 41 is a main filter having the function of catching bubbles existing in blood flowing through the blood passages 33. The second filter member 43 is an auxiliary filter having the function of catching bubbles in blood when the rotation speed of the blood pump located on the downstream of the oxygenator 1 is excessively higher due to some abnormality as described above and the bubbles have flowed through the first filter member 41. As in the foregoing, bubbles may flow through the first filter member 41 depending on the use condition (use environment) of the oxygenator 1. In this case, the second filter member 43 is effective in catching such bubbles.

The first filter member 41 is formed by a substantially rectangular, flat sheet-shaped member (hereinafter, also referred to simply as "sheet"), and is fixed to the housing 2 by being secured at its edges (four sides) through the partition walls 8 and 9 and the respective securing portions 7.

In the illustrated embodiment, the plane shape of the first filter member 41 is rectangular (or square). However, the plane shape of the first filter member 41 is not limited to this shape and may be a trapezoid, parallelogram, oval, elongated circle, or the like.

The first filter member 41 is formed by a flat sheet in the illustrated embodiment.

The first filter member 41 has a single surface in contact with a downstream surface (blood outlet portion side) of the hollow fiber membrane bundle 3 so as to cover substantially the entire surface. Providing the first filter member 41 in this manner makes it possible to make larger the effective area of the first filter member 41 and allow the first filter member 41 to exert sufficiently the capability of catching bubbles. In addition, when the effective area of the first filter member 41 is larger, even if the first filter member 41 is partly clogged (with adhesion of clots of blood, for example), it is possible to prevent (suppress) interference with the entire flow of blood.

The gap, that is, the blood outlet-side opening 25, is formed between the first filter member 41 and the housing 2 (see FIGS. 2 to 4). It is thus possible to suppress contact (close adhesion) of the first filter member 41 with the inner surface of the housing 2. Accordingly, the blood having flowed through the first filter member 41 can rather easily flow downward in the blood outlet-side opening 25 and smoothly flow toward the blood outlet port 28.

The second filter member 43 is opposed to the first filter member 41 with the blood outlet-side opening 25 between the two filter members 41, 43. In other words, the second filter member 43 is separated from the first filter member 41, and overlaps the first filter member 41 in a side view of the housing 2 (as seen from the axial direction of the blood outlet port 28). Further, the second filter member 43 is located upstream of the blood outlet port 28, that is, near the end portion of the square rectangular housing body 21 (housing 2).

As illustrated in FIG. 4 (also FIGS. 2 and 3), the second filter member 43 is formed by a substantially circular flat sheet-shaped member, and has a downstream surface fixed by a securing portion 11 to the inner peripheral surface of the blood outlet port 28. The securing portion 11 is formed by the same material as that for the partition walls 8 and 9 (potting material) or another adhesive. The second filter member 43 may be fixed by fusing (heat fusing, high-frequency fusing, ultrasonic fusing, or the like) or insert molding.

The oxygenator 1 having the thus arranged first filter member 41 and second filter member 43 is used in a posture illustrated in FIG. 2. In this case, the blood outlet port 28 is located at a vertically lower position at use of the oxygenator 1. Specifically, the lumen of the blood outlet port 28 communicates with the lower portion of the blood outlet-side opening 25. Accordingly, the blood having flowed through the first filter member 41 and entered into the blood outlet-side opening 25 flows downward in the blood outlet-side opening 25, flows through the second filter member 43, and then flows out from the blood outlet port 28 to the outside of the housing 2.

Even when bubbles exist in the blood flowing through the blood passages 33, the first filter member 41 can catch the bubbles. The bubbles caught by the first filter member 41 enter into the hollow fiber membranes 31 near the first filter member 41 by a difference in pressure between the blood passages 33 and the hollow fiber membranes 31 (gas passages 32), and as a result, the bubbles are removed from the blood passages 33.

Depending on the use status of the oxygenator 1, specifically, when the rotation speed of the blood pump mounted on the downstream of the oxygenator 1 is excessively higher due to some abnormality, the pressure at the blood passage side may be excessively lower than the pressure in the gas passages (the lumens of the hollow fiber membranes 31). In this case, gas emerges from the lumens of the hollow fiber membranes 31 into the blood passages, and then forms bubbles. At a connection portion between the hollow fiber membranes 31 and the first filter member 41, the bubbles flow through the first filter member 41.

However, even when some bubbles undesirably have flowed through the first filter member 41, the bubbles are caught by the second filter member 43 in a reliable manner. This makes it possible to prevent outflow of the from the blood outlet port 28 in a reliable manner.

Some of the bubbles having flowed through the first filter member 41 float in the blood outlet-side opening 25 and other bubbles move toward the blood outlet port 28. The former bubbles flow directly into the exhaust port 29, and then are discharged from the exhaust port 29. Meanwhile, the latter bubbles are caught by the second filter member 43, and float in the blood outlet-side opening 25 as with the former bubbles, and then are discharged from the exhaust port 29. Thus, any bubbles which have flowed through the first filter member 41 are prevented from being discharged from the blood outlet port 28. It can thus be said that the exhaust port 29 functions as portion of the bubble removal means 4.

By way of example, the first filter member 41 and the second filter member 43 may be configured in a form of mesh (net), woven cloth, non-woven cloth, or any combination of the foregoing ones. Among the foregoing forms, a mesh (net) form is preferred and a screen filter is in particular preferred. This makes it possible to catch bubbles in a reliable manner by the two filter members and facilitate smooth flow of the blood.

When the first filter 41 and the second filter member 43 are each configured in a mesh form, these members are preferably the same in mesh size. Although not particularly limited in this way, the mesh size is preferably equal to or less than 80 µm, more preferably about 15 to 60 µm, even more preferably 20 to 45 µm. This makes it possible to catch relatively fine bubbles without increasing the flow resistance of the blood and provide high efficiency of catching bubbles (removal capability).

The first filter member 41 and the second filter member 43 are preferably formed of the same material. The constituent material may be, for example, polyolefin such as polyamide, polyethylene, or polypropylene, polyester such as polyethylene terephthalate or polybutylene terephthalate, nylon, cellulose, polyurethane, aramid fiber, or the like. In particular, polyethylene terephthalate, polyethylene, or polyurethane are preferably used as constituent material for the filter members because these materials are excellent in resistance to blood clotting and are less prone to cause clogging.

The first filter member 41 and the second filter member 43 are each preferably hydrophilic. Specifically, the filter members are each preferably formed by a hydrophilic material or subjected to hydrophilicity process (for example, plasma treatment or the like). This facilitates removal of bubbles upon priming of the oxygenator 1. In addition, when the blood mixed with bubbles flows, the bubbles are further unlikely to flow, which more reliably prevents outflow of bubbles from the blood outlet port 28 with improvement of the filter members in bubble removal capability.

The first filter member 41 and the second filter member 43 may be each formed in a form of a single sheet (in particular, a mesh such as a screen filter) or two or more stacked sheets. When two or more sheets are stacked, the sheets are preferably different in at least one of conditions such as form, constituent material, mesh size, flat/non-flat state, plane shape, and the like. This is because combining the different conditions is advantageous in providing the filter members with a variety of (multiplicity) functions and further improving the bubble removal capability. For example, of the first filter member 41 and the second filter member 43, the first filter member 41 will be described as a representative. When the first filter member 41 is formed by two stacked meshes different in mesh size (the mesh with the larger mesh size is located on the upstream side), it is possible to first catch relatively large bubbles at the mesh with the larger mesh size and then catch fine bubbles having flowed through the mesh at the mesh with a smaller mesh size. This improves the bubble removal capability without increasing the flow resistance of the blood.

As illustrated in FIG. 4, the area of the second filter member 43 is smaller than the area of the first filter member 41. The second filter member 43 is an auxiliary filter for the first filter member 41 as a main filter, and thus even these filter members different in area can exert sufficient bubble catching capability.

Next, the heat exchange portion (heat exchanger) 1B will be described. The heat exchanger 1B includes the heat exchanger housing 5. The heat exchanger housing 5 is substantially cylinder-shaped and closed at upper and lower ends of the housing 5. A blood chamber 50 is located inside the heat exchanger housing 5. The heat exchanger housing 5 has a tubular heat medium inlet port 52 and a heat medium outlet port 53 protruding from a lower end (lower surface) of the housing 5. In addition, the heat exchanger housing 5 has a tubular blood inlet port 51 protruding from a lower portion at the left side of the housing 5 illustrated in FIG. 2. The lumen of the blood inlet port 51 communicates with the blood chamber 50.

An entirely cylindrical heat exchange body 54 is located in the heat exchanger housing 5. A circular cylindrical heat medium chamber forming member (circular cylindrical wall) 55 is arranged on an inner periphery of the heat exchange body 54, and a separation wall 56 inside the circular cylindrical heat medium chamber forming member separates the inner space of the heat medium chamber forming member 55 into an inlet-side heat medium chamber 57 and an outlet-side heat medium chamber 58. The heat medium chamber forming member 55 functions to form a heat medium chamber inside the heat exchange body 54 for temporarily reserving heat medium, and the function of restricting deformation of the cylindrical heat exchange body.

The heat medium chamber forming member 55 and the separation wall 56 are fixed to the heat exchanger housing 5 by fusing, adhering with an adhesive, or the like, for example. The heat medium chamber forming member 55 and the separation 56 may be separately or integrally formed.

The heat medium chamber forming member 55 has band-like openings 59a and 59b extending in the vertical direction and penetrating the wall portion of the heat medium chamber forming member 55. The openings 59a and 59b are opposed to each other with the separation wall 56 therebetween as seen in FIG. 3. The opening 59a communicates with the inlet-side heat medium chamber 57, and the opening 59b communicates with the outlet-side heat medium chamber 58.

The heat exchange body 54 may be in the form of a so-called bellows-type heat exchange body (bellows tube) as illustrated in FIG. 2. The bellows-type heat exchange body 54 includes a bellows forming portion with multiple hollow annular projections substantially parallel to the side surface of the axially central portion of the heat exchange body 54, and a cylindrical portion formed at opposite ends (upper and lower ends) of the heat exchange body 54 and having an inner diameter substantially equal to the inner diameter of the bellows forming portion. The heat exchange body 54 is formed by a metal material such as stainless steel or aluminum or a resin material such as polyethylene or polycarbonate. Metal materials such as stainless steel or aluminum are preferred from the viewpoint of strength and heat exchange efficiency. In particular, the bellows-type heat exchange body 54 is preferably formed by a metallic bellows tube in a corrugated form with multiple repeated convexes and concaves substantially orthogonal to the axial direction (central axis) of the heat exchange body 54.

Materials for the heat exchange housing 5, the heat medium chamber forming member 55, and the separation wall 56 may be, for example, polyolefin such as polyethylene or polypropylene, ester resin (for example, polyester such as polyethylene terephthalate or polybutylene terephthalate), styrene resin (for example, polystyrene, MS resin, or MBS resin), resin materials such as polycarbonate, various kinds of ceramics materials, metal materials, or the like.

A flow of heat medium in the heat exchange portion 1B of the oxygenator 1 will be described below with reference to FIGS. 1 to 3.

The heat medium flowing from the heat medium inlet port 52 first enters into the inlet-side heat medium chamber 57, flows into an outer peripheral side of the heat medium chamber forming member 55 through the opening 59a, spreads in substantially the entire outer periphery of the heat medium chamber forming member 55, and then enters into the multiple concaves in the bellows of the heat exchange body 54 (inside of the hollow annular projections). Accordingly, the heat exchange body 54 is heated or cooled in contact with the heat medium. Then, heat exchange (heating or cooling) is conducted between the heat exchange body 54 and the blood flowing on the outer peripheral side of the heat exchange body 54.

The heat medium used for heating or cooling of the heat exchange body 54 enters into the outlet-side heat medium chamber 58 through the opening 59b and then is discharged from the heat medium outlet port 53.

The illustrated embodiment shows the heat exchange portion 1B in the upstream of the oxygenating portion 1A, but the heat exchange portion 1B may also be provided downstream of the oxygenating portion 1A. Further, the heat exchange portion 1B may not be provided.

A flow of blood in the oxygenator 1 of this embodiment will now be described.

In the oxygenator 1, the blood flowing from the blood inlet port 51 flows into the blood chamber 50, that is, between the inner peripheral surface of the heat exchanger housing 5 and the heat exchange body 54, and contacts the outer surfaces of a plurality of hollow annular projections in the heat exchange body 54 to be subjected to heat exchange (heating or cooling). The blood thus having undergone heat exchange is collected on the downstream of the heat exchanger housing 50, and flows into the housing 2 of the oxygenating portion 1A through the blood inlet-side opening 24.

The blood having flowed through the blood inlet-side opening 24 flows through the blood passages 33 in the downstream direction. Meanwhile, gas (gaseous matter including oxygen) supplied from the gas inlet port 26 is distributed by the first chamber 221 into the gas passages 32 in the lumens of the hollow fiber membranes 31, flows through the gas passages 32, is accumulated in the second chamber 231, and then is discharged from the gas outlet port 27. The blood flowing through the blood passages 33 contacts the surfaces of the hollow fiber membranes 31 and is subjected to gas exchange (oxygenation and decarbonation) with the gas flowing through the gas passages 32.

When bubbles are mixed into the blood having undergone gas exchange, the bubbles are caught by the first filter member 41 and thus do not flow out to downstream of the first filter member 41. Even if the bubbles flow downstream of the first filter member 41 depending on the use condition as described above, the bubbles are caught by the second filter member 43. Thus, the discharge of the bubbles from the blood outlet port 28 is blocked in a reliable manner. The bubbles caught by the second filter member 43 float in the blood outlet-side opening 25 as described above, and are discharged from the discharge port 29.

The blood having thus undergone gas exchange and bubble removal flows out from the blood outlet port 28.

In the oxygenator 1 of this embodiment, it is preferred that blood-contacting surfaces (for example, the inner surface of the housing 2, the inner surface of the heat exchanger housing 5, the surface of the heat medium chamber forming member 55, the surface of the separation wall 56, and surfaces of the securing portions 7 and the partition walls 8 and 9 facing the blood passages 33) are made antithrombotic. The antithrombotic surfaces can be formed by being applied and fixed with an antithrombotic material to the surfaces. The antithrombotic material may be heparin, urokinase, HEMA-St-HEMA copolymer, poly-HEMA, and the like.

The oxygenator 1 is not particularly limited concerning the flow rate of blood flowing from the blood inlet port 51 because the flow rate of blood may be different depending on a patient's physique and an operation procedure. In general, the flow rate of blood is preferably about 0.1 to 2.0 L/min for infants and young children, and preferably about 2.0 to 5.0 L/min for school children, and preferably about 3.0 to 7.0 L/min for adults.

The oxygenator 1 is not particularly limited on the flow rate of gas supplied from the gas inlet port 26 because the flow rate of gas may be different depending on a patient's physique and an operation procedure. In general, the flow rate of gas is preferably about 0.05 to 4.0 L/min for infants and young children, and preferably about 1.0 to 10.0 L/min for school children, and preferably about 1.5 to 14.0 L/min for adults.

In addition, the concentration of oxygen in the gas supplied from the gas inlet port 26 is not limited to a specified value because the concentration of oxygen may be different depending on the metabolic amount of oxygen/carbon-dioxide gas of a patient under surgery. The concentration of oxygen can be 40 to 100%.

The maximum continuous operation time of the oxygenator 1 is also not limited to a certain time because the maximum continuous operation time may be different depending on a patient's condition and an operation procedure. In general, the maximum continuous operation time can be about 2 to 6 hours. In addition, the maximum continuous operation time of the oxygenator 1 may be as long as about 10 hours on rare occasions.

Figure 5:
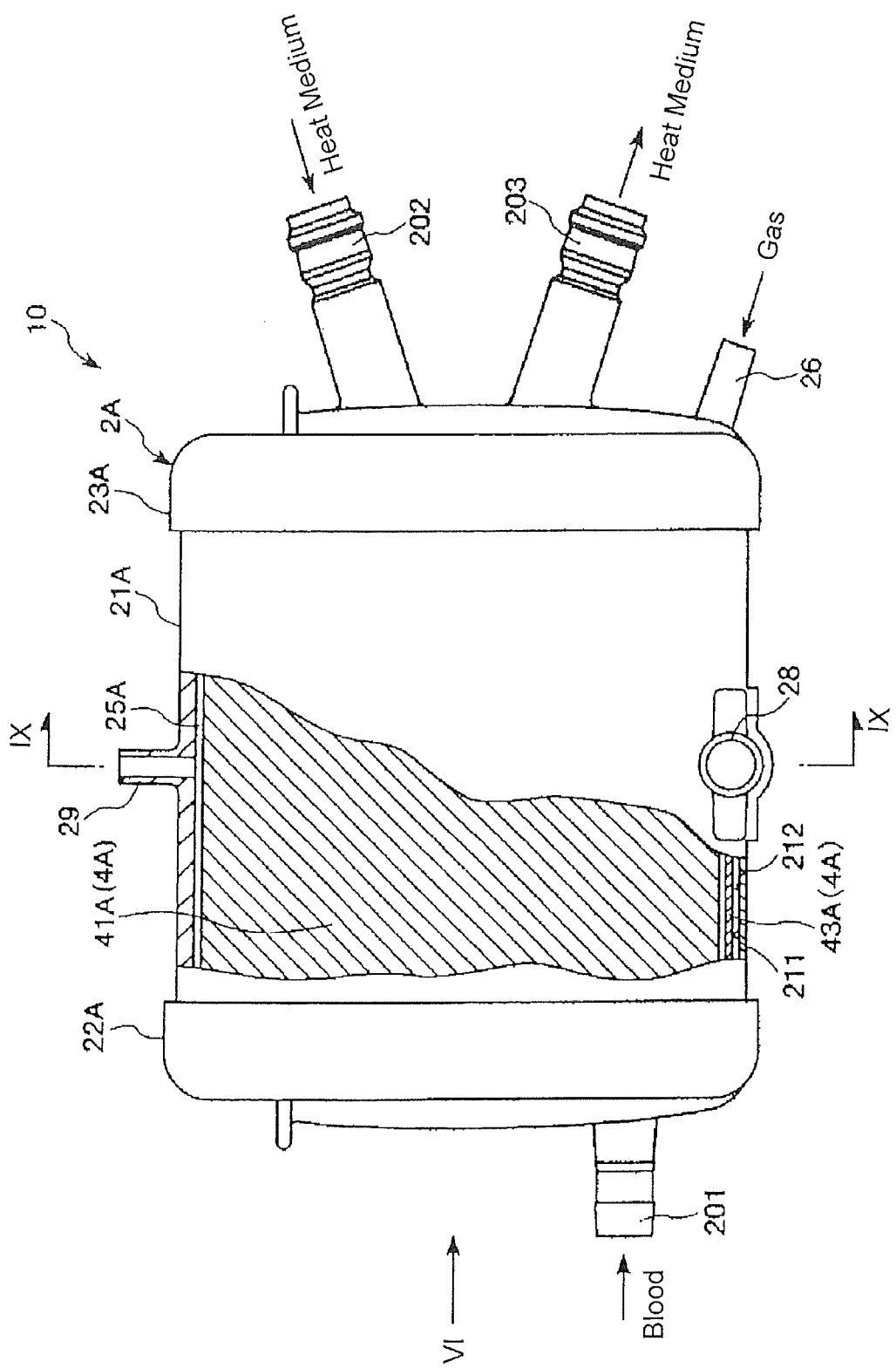
FIG. 5 is a plan view of a second embodiment of an oxygenator representing another example of the oxygenator disclosed here.
Figure 6:
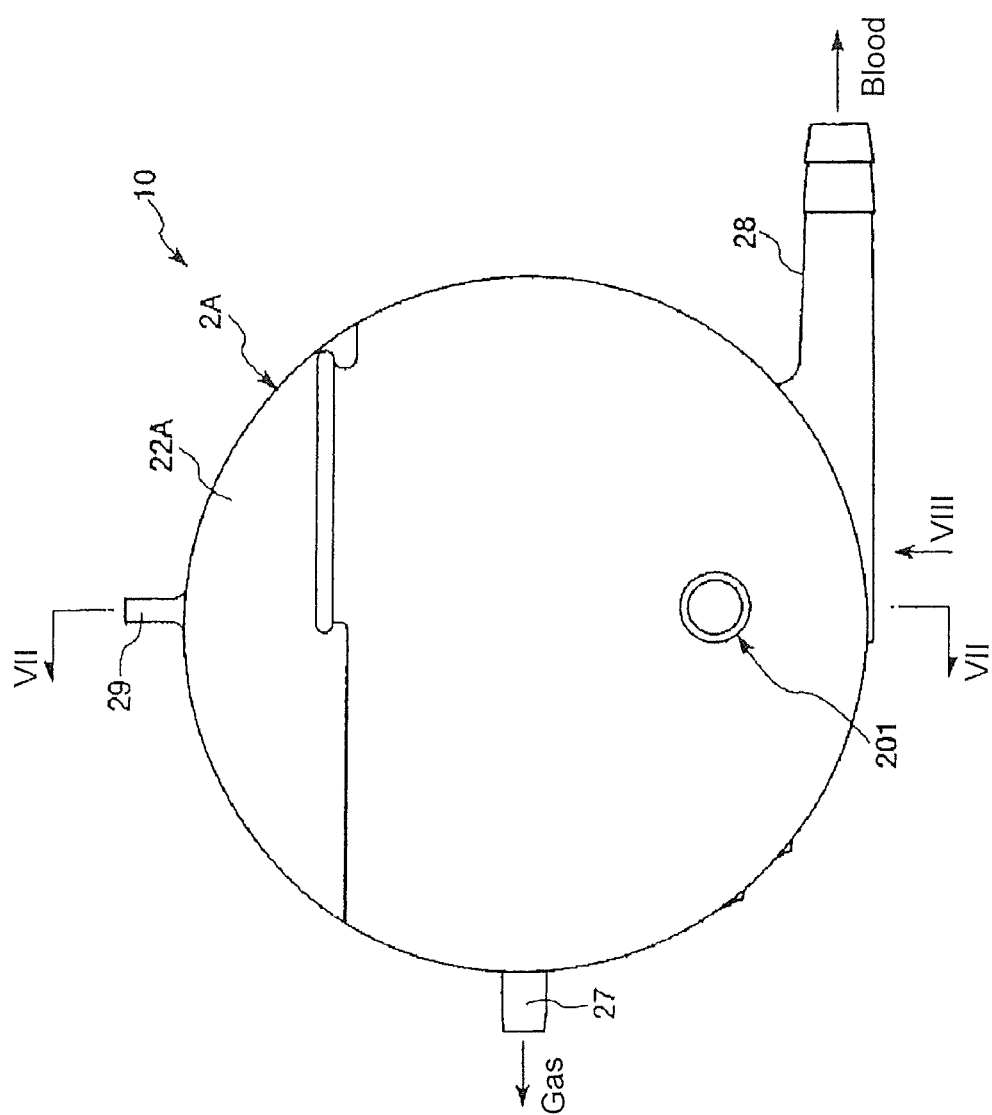
FIG. 6 is an end view of the oxygenator illustrated in FIG. 5 as seen from arrow VI-VI.
Figure 7:
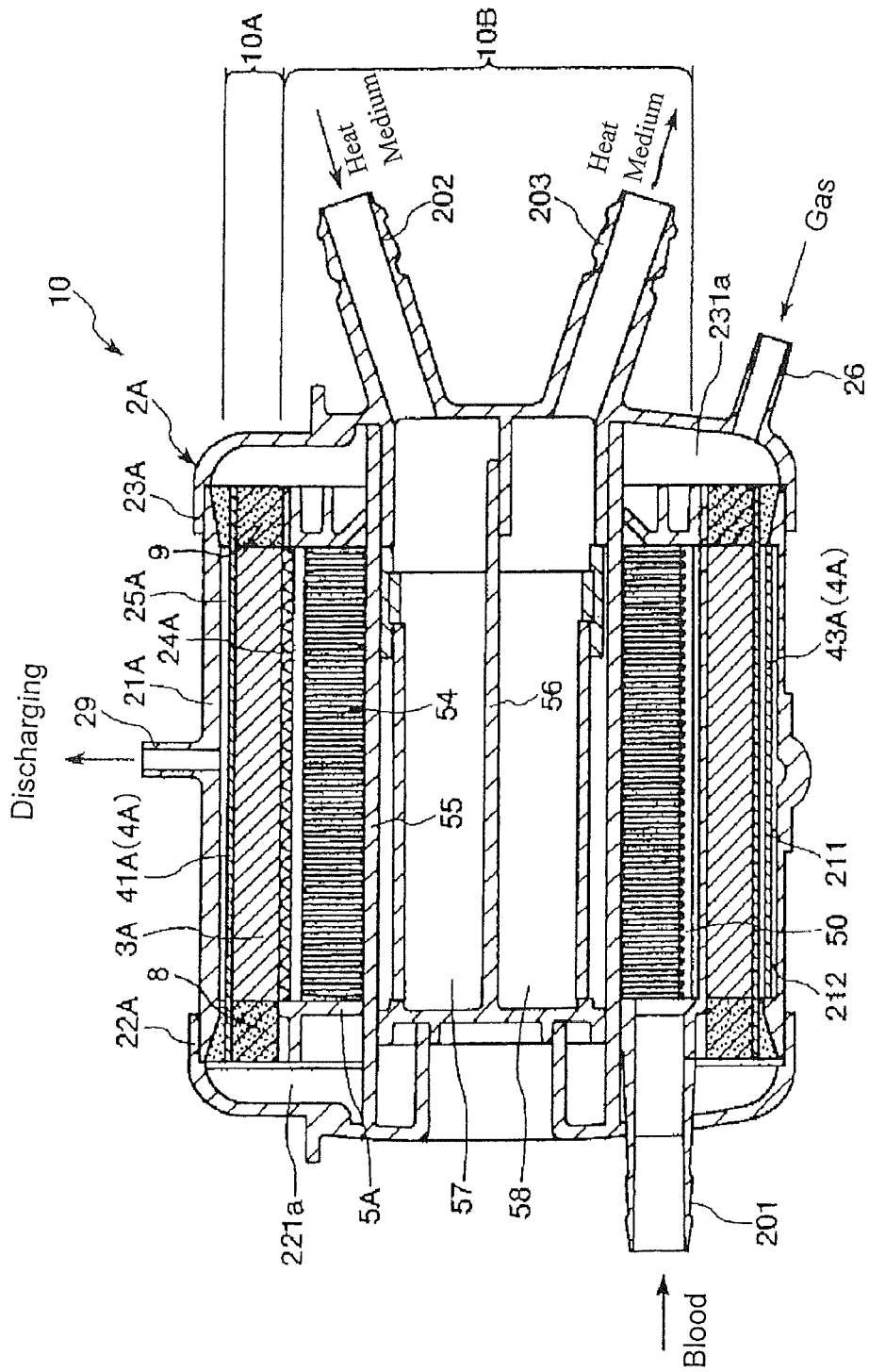
FIG. 7 is a cross-sectional view of the oxygenator taken along the section line VII-VII in FIG. 6.
Figure 8:
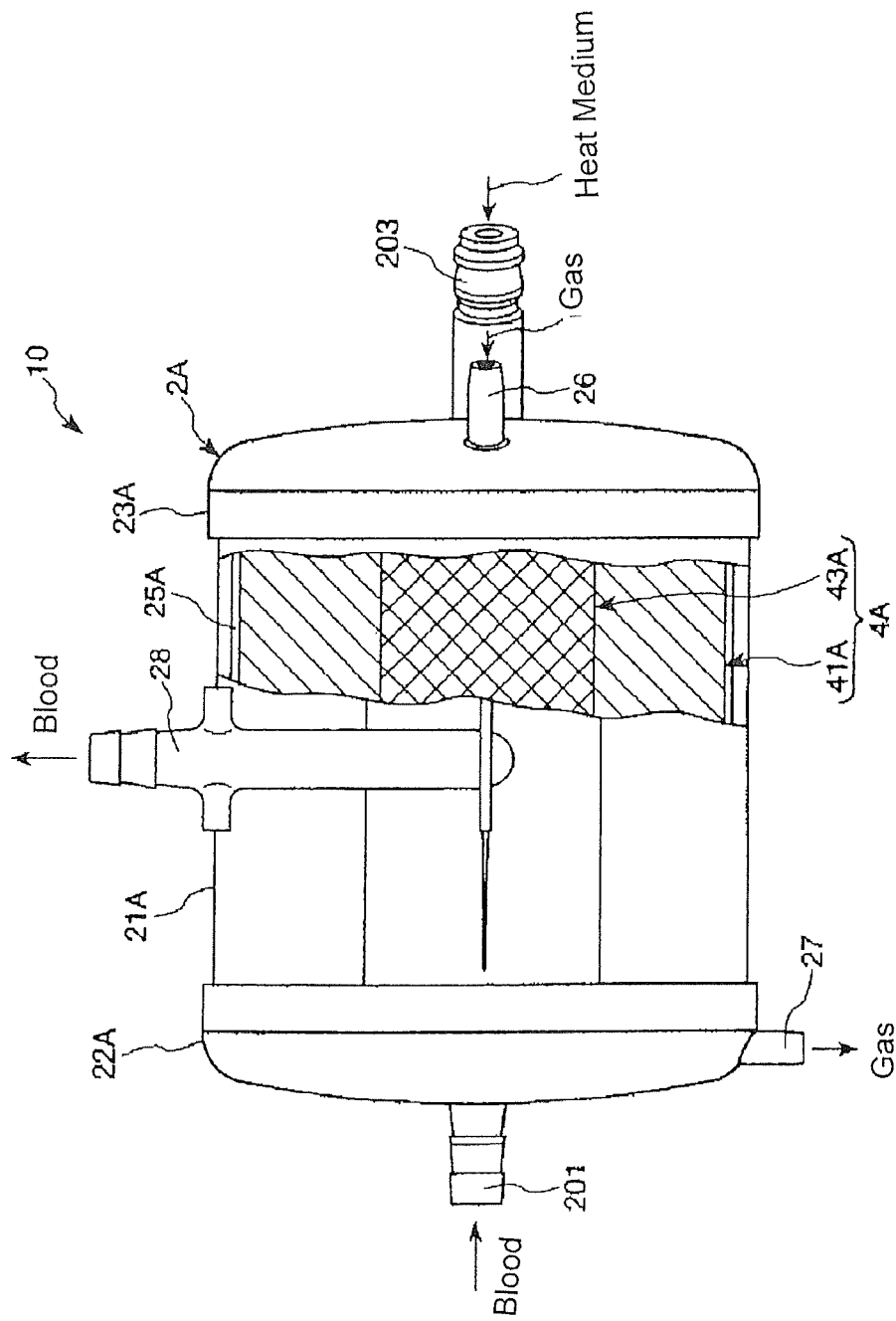
FIG. 8 is a said view of the oxygenator as seen from the direction of the arrow VIII in FIG. 6.

FIGS. 5-10 illustrate a second embodiment of an oxygenator representing another example of the oxygenator disclosed here. In FIGS. 5, 7 and 8, the left side is referred to as the "left" or "left side," and the right side is referred to as the "right" or "right side." In FIGS. 5-10, the inside of the oxygenator is referred to as the "blood inlet side" or "upstream," and the outside of the oxygenator is referred to as the "blood outlet side" or "downstream."

The following description of the second embodiment of the oxygenator will focus primarily on differences between this embodiment and the embodiment described above. Features of this second embodiment of the oxygenator that are the same as in the first oxygenator are designated by common reference numerals and a detailed description of such features is not repeated.

The second embodiment is the same as the first embodiment except for the entire or overall shape of the oxygenator.

The overall shape (outer shape) of the oxygenator 10 in the illustrated embodiment is substantially columnar. The oxygenator 10 is a heat exchanger-equipped oxygenator including a heat exchange portion (heat exchanger) 10B provided inside the oxygenator and configured in substantially the same manner as the heat exchanger portion 1B in the first embodiment, and an oxygenating portion 10A provided on an outer peripheral side of the heat exchange portion 10B and configured to conduct gas exchange with blood.

The oxygenator 1 has a housing 2A in which the oxygenating portion 10A and the heat exchange portion 10B are stored. The heat exchange portion 10B is further stored in a heat exchanger housing 5A in the housing 2A. The heat exchange portion 10B has opposite ends fixed to the housing 2A by the heat exchanger housing 5A.

The housing 2A is formed by a circular cylindrical housing body (hereinafter, referred to as "circular cylindrical housing body"), a dish-shaped first header (upper lid) 22A that closes a left end opening of the circular cylindrical housing body 21A, and a dish-shaped second header (lower lid) 23A that closes a right end opening of the circular cylindrical housing body 21A.

The circular cylindrical housing body 21A, the first header 22A, and the second header 23A are each formed by polyolefin such as polyethylene or polypropylene, ester resin (for example, polyester such as polyethylene terephthalate or polybutylene terephthalate), styrene resin (for example, polystyrene, MS resin, or MBS resin), resin materials such as polycarbonate, various kinds of ceramic materials, metal materials, or the like. The first header 22A and the second header 23A are secured to the circular cylindrical housing body 21A by adhesion means such as fusing, adhesion using an adhesive, or the like.

A tubular blood outlet port 28 is formed at an outer peripheral portion of the circular cylindrical housing body 21A. The blood outlet port 28 protrudes in substantially the direction of tangent to the outer peripheral surface of the circular cylindrical housing body 21A (see FIG. 9).

A tubular exhaust port (exhaust outlet) 29 is formed at the outer peripheral portion of the circular cylindrical housing body 21A in an axially intermediate portion of the circular cylindrical housing body 21A. When the oxygenator 10 is used, the oxygenator 10 is oriented so that the exhaust port 29 is located at the upper portion of the circular cylindrical housing body 21A and protrudes upward (see FIGS. 5 to 7 and 9).

A tubular blood inlet portion 201 and a gas outlet port 27 protrude from the first header 22A. The blood inlet portion 201 is formed on an end surface of the first header 22A such that a central axis of the blood inlet portion 201 is located eccentrically with respect to the center of the first header 22A. The gas outlet port 27 is formed at an outer peripheral portion of the first header 22A such that a central axis of the gas outlet port 27 crosses the center of the first header 22A as seen in FIG. 6.

A tubular gas inlet port 26, a heat medium inlet port 202, and a heat medium outlet port 203 protrude from the second header 23A. The gas inlet portion 26 is formed at an edge portion of an end surface of the second header 23A. The heat medium inlet port 202 and the heat medium outlet port 203 are each formed at substantially the center portion of the end surface of the second header 23A. Center lines of the heat medium inlet port 202 and the heat medium outlet port 203 are slightly inclined with respect to the center line of the second header 23A.

The overall shape of the housing 2A is not necessarily a complete column, but the housing 2A may be partially cut away or provided with a different-shaped portion.

Figure 9:
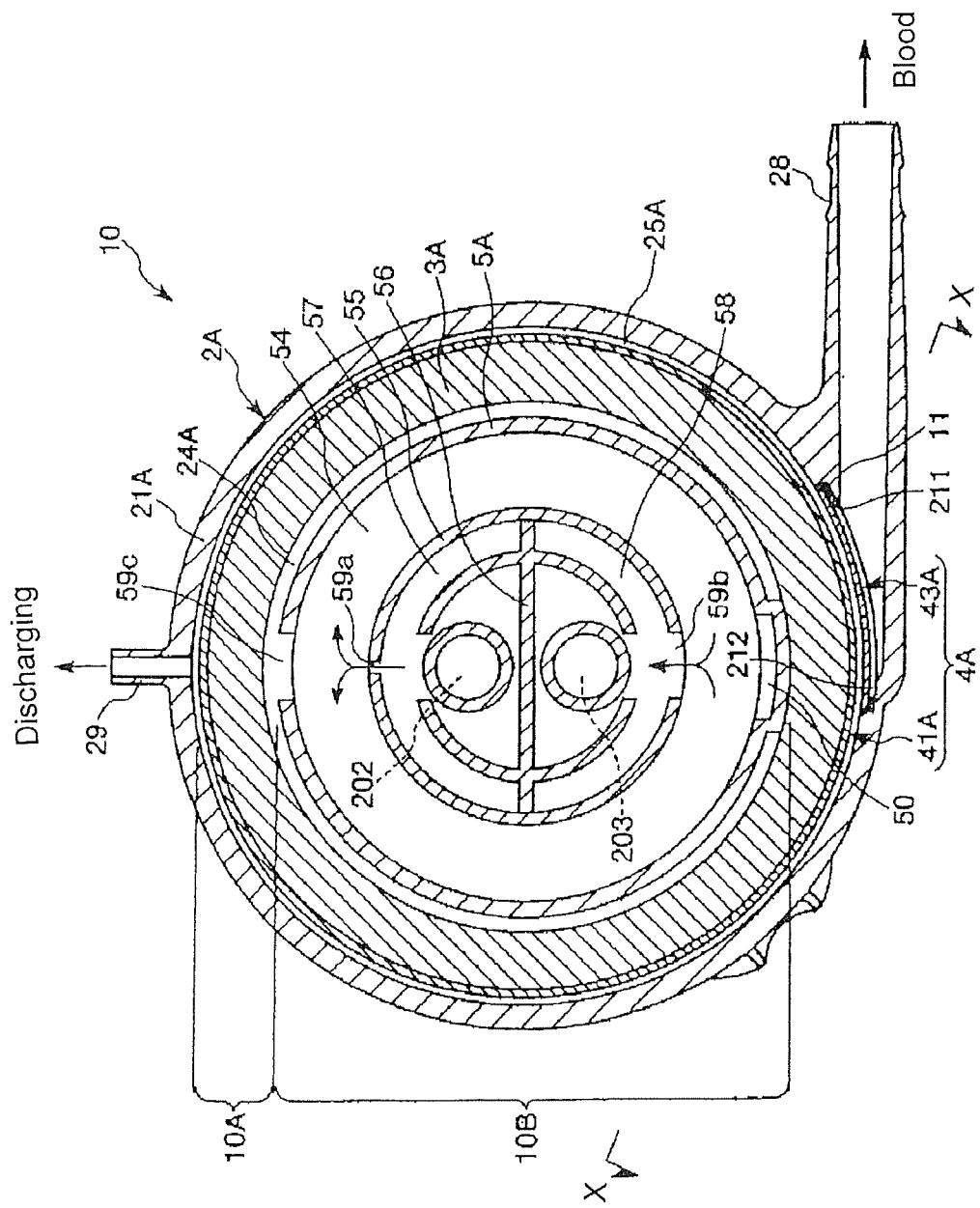
FIG. 9 is a cross-sectional view of the oxygenator taken along the section line IX-IX in FIG. 5.

As illustrated in FIGS. 7 and 9, the housing 2A stores an oxygenating portion 10A shaped in a circular cylinder following an inner peripheral surface of the housing 2A. The oxygenating portion 10A is formed by a circular cylindrical hollow fiber membrane bundle 3A, and a first filter member 41A and a second filter member 43A as bubble removal means 4A provided on an outer peripheral side (blood outlet portion side) of the hollow fiber membrane bundle 3A. The layer 3A and the filter members 41A, 43A are arranged from the blood inlet side in the following order—the hollow fiber membrane bundle 3A, the first filter member 41A, and the second filter member 43A.

Figure 10:
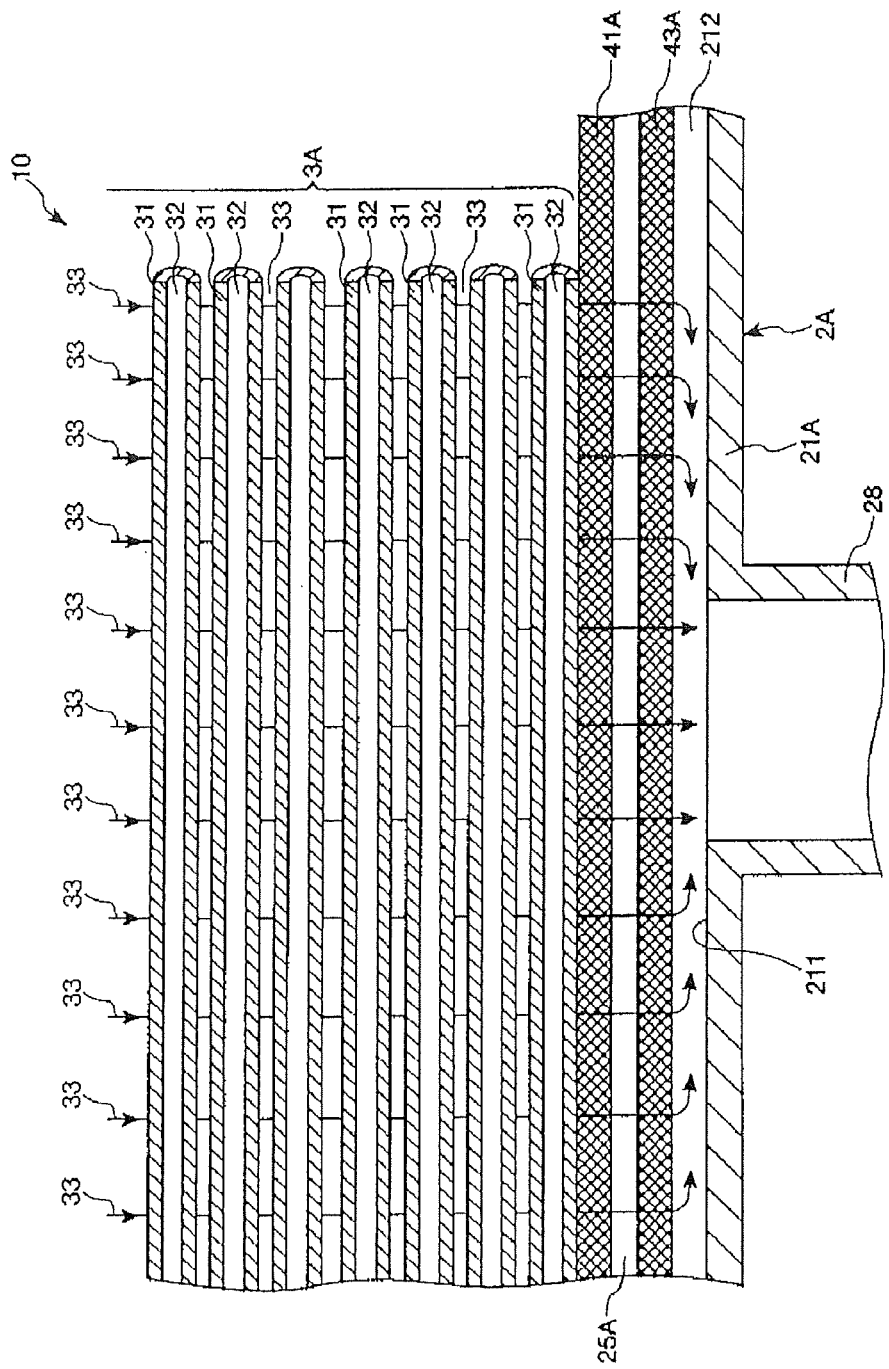
FIG. 10 is a cross-sectional view of the oxygenator taken along the section line X-X in FIG. 9.

As illustrated FIG. 10, the hollow fiber membrane bundle 3A includes multiple integrated hollow fiber membranes 31 having a gas exchange function. Most of the hollow fiber membranes 31 constituting the hollow fiber membrane bundle 3A are substantially parallel to the central axis of the housing 2A.

The arrangement pattern, arrangement direction, and the like of the hollow fiber membranes 31 in the hollow fiber membrane bundle 3A are not limited to the aforementioned ones. For example, the hollow fiber membranes 31 may be arranged perpendicular to the central axis of the housing 2A, the hollow fiber membranes 31 may have portions at which the hollow fiber membranes 31 obliquely intersect one another (crossing portions), all or some of the hollow fiber membranes 31 may be curved, or all or some of the hollow fiber membranes 31 may be arranged in a corrugated, helical, spiral, or annular form.

As illustrated in FIG. 7, opposite end portions (left end portion and right end portion) of the hollow fiber membranes 31 are fixed to the inner surface of the circular cylindrical housing body 21A by the partition walls 8 and 9.

The hollow fiber membrane bundle 3A is filled between the circular cylindrical housing body 21A and the heat exchange portion 10B substantially without space, and thus the hollow fiber membrane bundle 3A is entirely shaped in substantially a circular cylinder. This provides high efficiency of filling the hollow fiber membranes 31 into the similarly shaped circular cylindrical housing body 21A (with less dead space), which contributes to smaller size and higher performance of the oxygenating portion 10A.

Although not particularly limited, the thickness of the hollow fiber membrane bundle 3A (horizontal length in FIG. 9) is preferably about 2 to 100 mm, more preferably about 3 to 30 mm.

The hollow fiber membranes 31 are exposed between the partition walls 8 and 9 in the housing 2A to form blood passages 33 outside the hollow fiber membranes 31, that is, in the gaps between the hollow fiber membranes 31 to allow blood to flow from the upper to lower sides in FIG. 10.

On the upstream of the blood passages 33 (on an upstream-side surface of the hollow fiber membrane bundle 3A), that is, between the oxygenating portion 10A and the heat exchange portion 10B, a circular cylindrical blood inlet-side opening (blood inlet-side space) 24A is formed as a blood inlet portion for blood flowing from the blood inlet portion 201 (see FIGS. 7 and 9).

The blood having flown into the blood inlet-side opening 24A flows in the circumferential and longitudinal directions of the blood inlet-side opening 24A. Thus, the blood spreads in the entire blood inlet-side opening 24A. Accordingly, it is possible to transfer efficiently blood from the heat exchange portion 10B to the oxygenating portion 10A.

On the downstream of the blood passages 33 (on the downstream-side surface of the hollow fiber membrane bundle 3A), a circular cylindrical gap is formed between an outer peripheral surface of the first filter member 41A (described later) and the inner peripheral surface of the square cylindrical housing body 21A. The gap constitutes a blood outlet-side opening (blood outlet-side space) 25A. The blood outlet-side opening 25A and the blood outlet port 28 communicating with the blood outlet-side opening 25A constitute a blood outlet portion. The blood outlet portion with the blood outlet-side opening 25A provides a space for the blood having flowed through the first filter member 41A to flow toward the blood outlet port 28, thereby allowing smooth discharge of blood.

The hollow fiber membrane bundle 3A, the first filter member 41A, and the blood passages 33 are present between the blood inlet-side opening 24A and the blood outlet-side opening 25A.

As illustrated in FIG. 9, the blood outlet-side opening 25A communicates with the discharge port 29 projecting from the circular cylindrical housing body 21A.

In the case where a blood pump for suctioning blood from a patient's body is mounted downstream of the oxygenator 10 (see FIGS. 11 and 12), and the rotation speed of the blood pump is excessively higher due to some abnormality, when the blood flows into the oxygenator 10, bubbles in the blood may flow through the first filter member 41A. However, the bubbles are caught at the second filter member 43A and then are discharged via the discharge port 29. This discharge makes it possible to remove the bubbles from the oxygenator 10.

Since the bubbles can be caught at the oxygenator 10, the extracorporeal circulation including the oxygenator 10 does not need a bubble removal device that is mounted in conventional extracorporeal circuits. That is, the oxygenator here is devoid of a bubble removal device provided in the extracorporeal circuit. Accordingly, when no bubble removal device is provided as described above, it is possible to suppress the amount of blood extracorporeally circulating.

As described above, the bubble removal means 4A with the function of catching bubbles in blood and removing the same from the blood, is provided on the downstream (blood outlet portion side) of the hollow fiber membrane bundle 3A. The bubble removal means 4A has the first filter member 41A and the second filter member 43A located downstream of the first filter member 41A.

The first filter member 41A is a main filter having the function of catching bubbles existing in blood flowing through the blood passages 33. The second filter member 43A is an auxiliary filter having the function of catching bubbles in blood when the rotation speed of the blood pump located downstream of the oxygenator 10 is excessively higher due to some abnormality as described above and the bubbles have flowed (been transmitted) through the first filter member 41. As in the foregoing, bubbles may flow through the first filter member 41A depending on the use condition (use environment) of the oxygenator 10. In this case, the second filter member 43A is effective in catching such bubbles.

The first filter member 41A is formed by a substantially rectangular, flat sheet-shaped member (hereinafter, also referred to simply as "sheet"). The first filter member 41A is formed by winding a substantially rectangular sheet-shaped member (hereinafter, referred also to as simply "sheet") in a columnar shape. The first filter member 41A has opposite end portions adhered and fixed by the partition walls 8 and 9 to the housing 2A (see FIG. 7).

The first filter member 41A has an inner peripheral surface in contact (direct contact) with downstream surface (blood outlet portion side) of the hollow fiber membrane bundle 3A so as to cover substantially the entire downstream surface. Providing the first filter member 41A in this manner makes it possible to make larger the effective area of the first filter member 41A and allow the first filter member 41A to exert sufficiently the capability of catching bubbles. In addition, when the effective area of the first filter member 41A is larger, even if the first filter member 41A is partly clogged (with adhesion of clots of blood, for example), it is possible to prevent (suppress) interference with the entire flow of blood.

In the illustrated embodiment, the first filter member 41A has a substantially constant outer diameter.

As illustrated in FIG. 9, downstream of the first filter member 41A, the second filter member 43A is opposed to the first filter member 41A via the blood outlet-side opening 25A. As illustrated in FIG. 8, the second filter member 43A overlaps the first filter member 41A in a side view of the circular cylindrical housing body 21A (housing 2), that is, as seen from the blood outlet port 28 side. Accordingly, it is possible to catch blood quickly by the second filter member 43A immediately after flow of the bubbles through the first filter member 41A.

The area of the second filter member 43A is smaller than the area of the first filter member 41A (see FIG. 8). The filter members are thus different in size because the second filter member 43A can exert a sufficient bubble catching function with the blood outlet port 28 covered near an end on the circular cylindrical housing body 21A side (see FIGS. 9 and 10).

As illustrated in FIGS. 9 and 10, the second filter member 43A is located at a concave portion (recessed portion) 211 formed at an inner peripheral portion of the circular cylindrical housing body 21A. The concave portion 211 has a depth larger than the thickness of the second filter member 43A. The second filter member 43A placed at the concave portion 211 is curved in an arc toward the downstream (blood outlet port 28 side) with the same curvature as that of the inner peripheral portion of the circular cylindrical housing body 21A. Thus, the shape of the second filter member 43A as seen from the axial direction of the circular cylindrical housing body 21, that is, the shape of the second filter member 43A illustrated in FIG. 9 forms one continuous circle together with the inner peripheral portion of the cylindrical housing body 21. Stated differently, the second filter member 43A is configured as a continuation of the curvature of the inner surface of the cylindrical housing body 21 so that the radius of curvature of the second filter member 43A is the same as the radius of curvature of the inner surface of the cylindrical housing body 21. Therefore, a smooth arc-like curved line is formed without any level difference at a boundary portion between the second filter member 43A and the inner peripheral portion of the circular cylindrical housing body 21A. Accordingly, it is possible to prevent that the bubbles caught by the second filter member 43A are retained (snagged) at a portion with a level difference, for example, and allow the bubble to float toward the discharge port 29. It is thus possible to discharge the floating bubbles from the discharge port 29.

When the second filter member 43A is curved in an arc, the effective area of the second filter member 43A can be made large as much as possible and the second filter member 43A can exert sufficiently the bubble catching capability.

As illustrated in FIG. 5 (and FIGS. 7, 9 and 10), a gap 212 exists between a bottom of the concave portion 211 and the second filter member 43A. The gap 212 functions as a passage for the blood having flowed through the second filter member 43A (see FIG. 10). Then, the blood having flowed through the gap 212 can travel toward the blood outlet port 28.

The oxygenator 10 having the thus arranged first filter member 41A and second filter member 43A is used in a posture illustrated in FIGS. 5 to 7 and 9. In this case, the blood outlet port 28 is located at a vertically lower position at use of the oxygenator 10. Specifically, the lumen of the blood outlet port 28 communicates with the lower portion of the blood outlet-side opening 25A. Accordingly, the blood having flowed through the first filter member 41A and entered into the blood outlet-side opening 25A flows toward the blood outlet port 28 in the blood outlet-side opening 25A, flows through the second filter member 43A, and then flows out from the blood outlet port 28 to the outside of the housing 2. The discharge port 29 is located at a vertically upper position.

Even when bubbles exist in the blood flowing through the blood passages 33, the first filter member 41A can catch the bubbles. The bubbles caught by the first filter member 41A enter into the hollow fiber membranes 31 near the first filter member 41A by a difference in pressure between the blood passages 33 and the hollow fiber membranes 31, and as a result, the bubbles are removed from the blood passages 33.

Depending on the use status of the oxygenator 10, specifically, when the rotation speed of the blood pump mounted on the downstream of the oxygenator 10 is excessively higher due to some abnormality, the pressure at the blood passage side may be excessively lower than the pressure in the gas passages (the lumens of the hollow fiber membranes 31). In this case, gas emerges from the lumens of the hollow fiber membranes 31 into the blood passages, and then forms bubbles. At a connection portion between the hollow fiber membranes 31 and the first filter member 41, the bubbles flow through the first filter member 41.

However, even when some bubbles undesirably have flowed through the first filter member 41A, the bubbles are caught by the second filter member 43A in a reliable manner. This makes it possible to prevent outflow of the from the blood outlet port 28 in a reliable manner.

Figure 12:
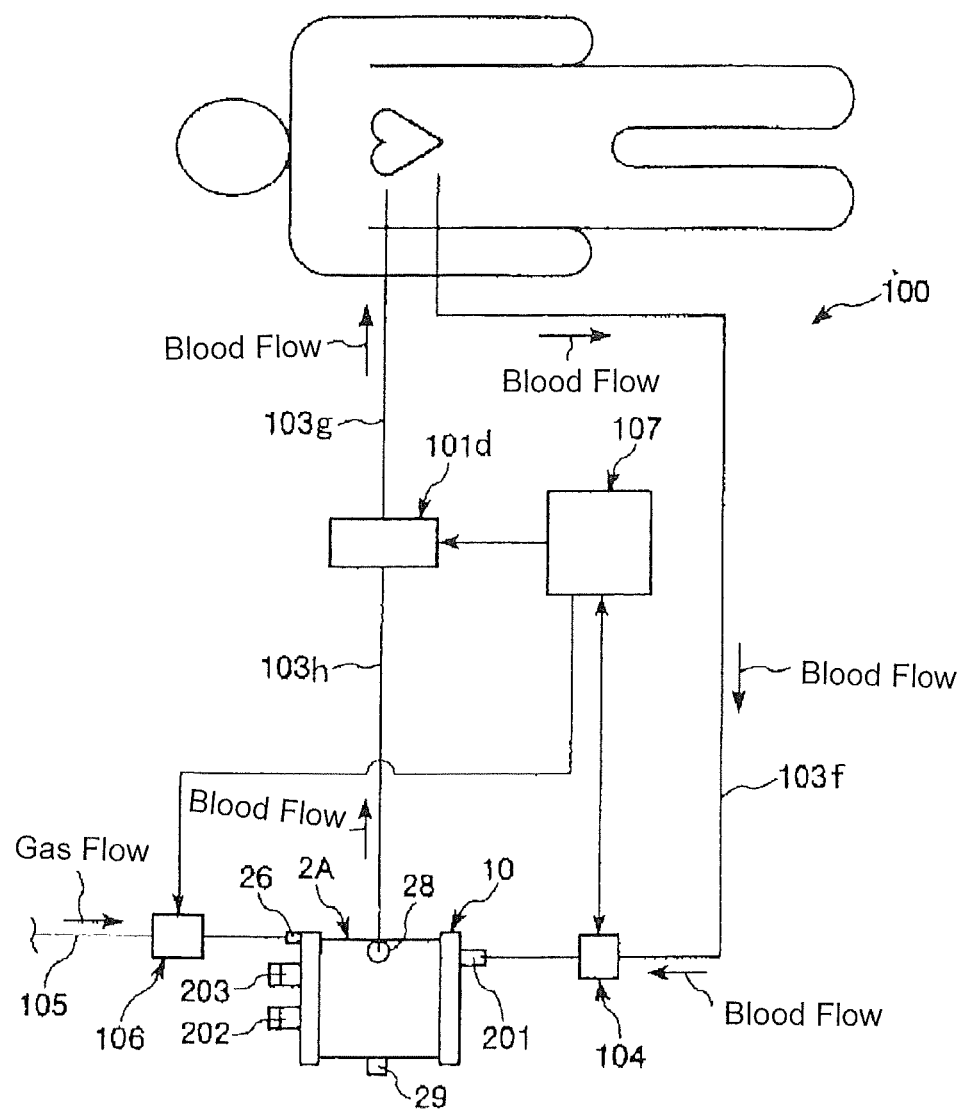
FIG. 12 is a schematic view of a second embodiment of an extracorporeal circuit representing another example of the extracorporeal circuit disclosed here.

For example, when an extracorporeal circuit 100 is configured as illustrated in FIG. 12, the blood pump 101 is located on the downstream of the oxygenator 10. Accordingly, if the rotation speed of the blood pump 101 is higher than a prescribed value or the circuit located on the upstream of the oxygenator 10 is closed for some reason, the pressure on the blood passage side may be lower than the pressure on the gas passage side (the lumens of the hollow fiber membranes 31) in the oxygenator 10. At that time, gas in the lumens of the hollow fiber membranes 31 emerges as bubbles on the blood passage side. At the portion of contact between the hollow fiber membranes 31 and the first filter member 41A, the bubbles flow through the hollow fiber membranes 31 and the first filter member 41A, and then flow toward a patient's body. To catch the bubbles, the second filter member 43A is provided on the downstream of the first filter member 41A at a position separated or spaced from the first filter member 41A to catch the bubbles having flowed through the first filter member 41A and prevent flow of the bubbles into a patient's body.

Some of the bubbles having flowed through the first filter member 41 float in the blood outlet-side opening 25 and others move toward the blood outlet port 28. The former bubbles flow directly into the exhaust port 29, and then are discharged from the exhaust port 29. Meanwhile, the latter bubbles are caught by the second filter member 43A, and float in the blood outlet-side opening 25 as with the former bubbles, and then are discharged from the exhaust port 29. The oxygenator thus prevents any of the bubbles having flowed through the first filter member 41A being discharged from or though the blood outlet port 28. It can be said that the exhaust port 29 functions as portion of the bubble removal means 4.

As illustrated in FIG. 7, a first chamber 221a is defined by the first header 22A, the partition wall 8, and the heat exchanger housing 5A and the heat medium chamber forming member 55 of the heat exchange portion 10B. The first chamber 221a is a gas outlet chamber from which gas flows out. The hollow fiber membranes 31 have left end openings open to and communicating with the first chamber 221a.

A second chamber 231a is defined by the second header 23A, the partition wall 9, and the heat exchanger housing 5A and the heat medium chamber forming member 55 of the heat exchange portion 10B. The second chamber 231a is a gas inlet chamber into which gas flows. The hollow fiber membranes 31 have right end openings open to and communicating with the second chamber 231a.

Lumens of the hollow fiber membranes 31 form gas passages 32 through which gas flows. The gas inlet port 26 and the second chamber 231a constitute a gas inlet portion located upstream of the gas passages 32. The gas outlet port 27 and the first chamber 221a constitute a gas outlet portion located downstream of the gas passages 32.

As described above, the heat exchange portion 10B is provided inside the oxygenating portion 10A. The heat exchange portion 10B is configured in substantially the same manner as the heat exchange portion 1B described above and so a detailed description will not be repeated.

Placing the heat exchange portion 10B inside the oxygenating portion 10A provides the following advantages. First, the oxygenating portion 10A and the heat exchange portion 10B can be efficiently stored in one housing 2A with less dead space, thereby to realize efficient gas exchange at the small-sized oxygenator 10. Second, the oxygenating portion 10A and the heat exchange portion 10B are closer to each other than those in the first embodiment, which allows the blood having undergone heat exchange at the heat exchange portion 10B to flow quickly into the oxygenating portion 10A. This makes it possible to minimize the amount of blood filled into the blood inlet-side opening 24A (blood passages 33) connecting the heat exchange portion 10B and the oxygenating portion 10A. Third, the blood having undergone heat exchange at the heat exchange portion 10B can flow quickly into the oxygenating portion 10A without being subjected to heat release or heat absorption.

Next, a flow of blood in the oxygenator 10 of this second embodiment will be described.

In the oxygenator 10, the blood flowing from the blood inlet port 201 flows into the blood chamber 50, that is, between the inner peripheral surface of the heat exchanger housing 5A and the heat exchange body 54, and contacts the outer surfaces of a plurality of hollow annular projections in the heat exchange body 54 to be subjected to heat exchange (heating or cooling). The blood thus having undergone heat exchange sequentially flows through the opening 59c formed at the upper portion of the heat exchanger housing 5A and the blood inlet-side opening 24A in sequence, and flows into the housing 2A of the oxygenating portion 10A.

The blood having flowed through the blood inlet-side opening 24A flows through the blood passages 33 in the downstream direction. Meanwhile, gas (gaseous matter including oxygen) supplied from the gas inlet port 26 is distributed by the second chamber 231a into the gas passages 32 in the lumens of the hollow fiber membranes 31, flows through the gas passages 32, is accumulated in the first chamber 221a, and then is discharged from the gas outlet port 27. The blood flowing through the blood passages 33 contacts the surfaces of the hollow fiber membranes 31 and is subjected to gas exchange (oxygenation and decarbonation) with the gas flowing through the gas passages 32.

When bubbles are mixed into the blood having undergone gas exchange, the bubbles are caught by the first filter member 41A and thus do not flow out to downstream of the first filter member 41A. Even if the bubbles flow downstream of the first filter member 41A depending on the use condition as described above, the bubbles are caught by the second filter member 43A. Thus, the discharge of the bubbles from the blood outlet port 28 is blocked in a reliable manner. The bubbles caught by the second filter member 43A float in the blood outlet-side opening 25A as described above, and are discharged from the discharge port 29.

The blood having thus undergone gas exchange and bubble removal flows out from the blood outlet port 28.

Figure 11:
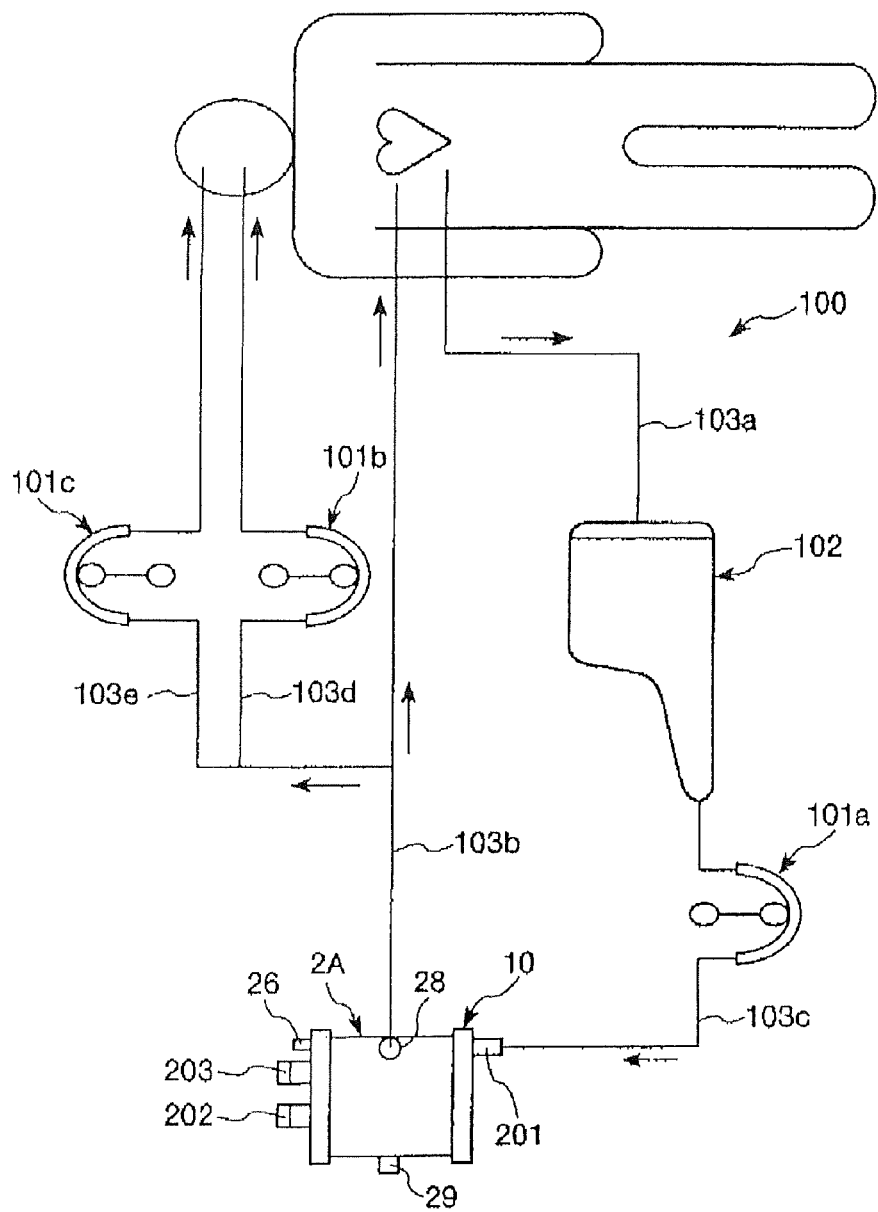
FIG. 11 is a schematic view of a first embodiment of an extracorporeal circuit representing an example of the extracorporeal circuit disclosed here.

FIG. 11 is a schematic diagram of a first embodiment of an extracorporeal circuit or extracorporeal circulation disclosed here.

The extracorporeal circuit (extracorporeal circulation circuit) 100 of the embodiment is used for brain-isolated extracorporeal circulation. The extracorporeal circuit 100 includes the oxygenator 1 of the first embodiment or the oxygenator 10 of the second embodiment. In the configuration illustrated in FIG. 11, the extracorporeal circuit 100 includes the oxygenator 10 of the second embodiment. Besides the oxygenator 10, the extracorporeal circuit 100 illustrated in FIG. 11 includes a first blood pump 101a, second blood pumps 101b and 101c, and a reservoir (blood reservoir) 102. From the upstream, the reservoir 102, the first blood pump 101a, the oxygenator 10, and the second blood pumps 101b and 101c are arranged in this order.

The reservoir 102 is connected to a patient's heart (great vein or vena cava) via a tube 103a as a blood removal line to reserve temporarily blood from the great vein or vena cava.

The oxygenator 10 is connected to a patient's aorta via a tube 103b as a blood transmission line to return the blood having undergone gas exchange at the oxygenator 10 to the aorta.

The reservoir 102 and the oxygenator 10 are connected together via a tube 103c. The first blood pump 101a is arranged in an intermediate portion of the tube 103c. The first blood pump 101a is a blood pump that is provided on the upstream of the oxygenator 10 to transfer blood for extracorporeal circulation.

Two tubes 103d and 103e branch from an intermediate portion of the tube 103b. The tubes 103d and 103e are blood transmission lines to transfer blood having undergone gas exchange at the oxygenator 10 to the head of a patient. The second blood pump 101b is arranged in an intermediate portion of the tube 103d, and the second blood pump 101c is arranged in an intermediate portion of the tube 103e.

The second blood pumps 101b and 101c are blood pumps provided on the upstream of the oxygenator 10 to transfer blood for extracorporeal circulation.

In the thus configured extracorporeal circuit 100, the blood transferring force of the second blood pumps 101b and 101c may exceed the blood transferring force of the first blood pump 101a depending on the operating state of the second blood pumps 101b and 101c. In this case, when the rotation speed of the second blood pumps 101b and 101c on the downstream of the oxygenator 10 is excessively high due to some abnormality as described above, that is, when the amount of blood transferred by the second blood pumps 101b and 101c on the downstream of the oxygenator 10 is relatively larger than that of the first blood pump 101a on the upstream of the oxygenator 10, the pressure in the blood passages 33 may be excessively lower than the internal pressure in the hollow fiber membranes 31 (gas passages 32). In this case, gas in the lumens of the hollow fiber membranes 31 may enter into the blood passages 33 and emerge as bubbles. At that time, the bubbles flow through the first filter member 41A at a place of close contact between the hollow fiber membranes 31 and the first filter member 41A. However, the bubbles having flowed through the first filter member 41A are reliably caught by the second filter member 43A and discharged from the discharge port 29. Thus, it is reliably prevented that the bubbles remain mixed in the blood and flow out form the blood outlet port 28, and then are transferred to the downstream of the oxygenator 10, that is, a patient's body.

In conventional extracorporeal circuits, an arterial filter is provided in front of a patient (downstream of the extracorporeal circuit) to prevent an inflow of bubbles into a patient's body. In the extracorporeal circuit 100 disclosed here by way of example, bubbles are removed at the oxygenator 10, which eliminates the need for an arterial filter. Accordingly, it is possible to suppress the amount of blood extracorporeally circulating by the elimination of an arterial filter.

In the configuration illustrated in FIG. 11, the number of the second pumps in the extracorporeal circuit 100 is two. However, the number of the second pumps is not limited to this but may be one or three or more.

Figure 13:
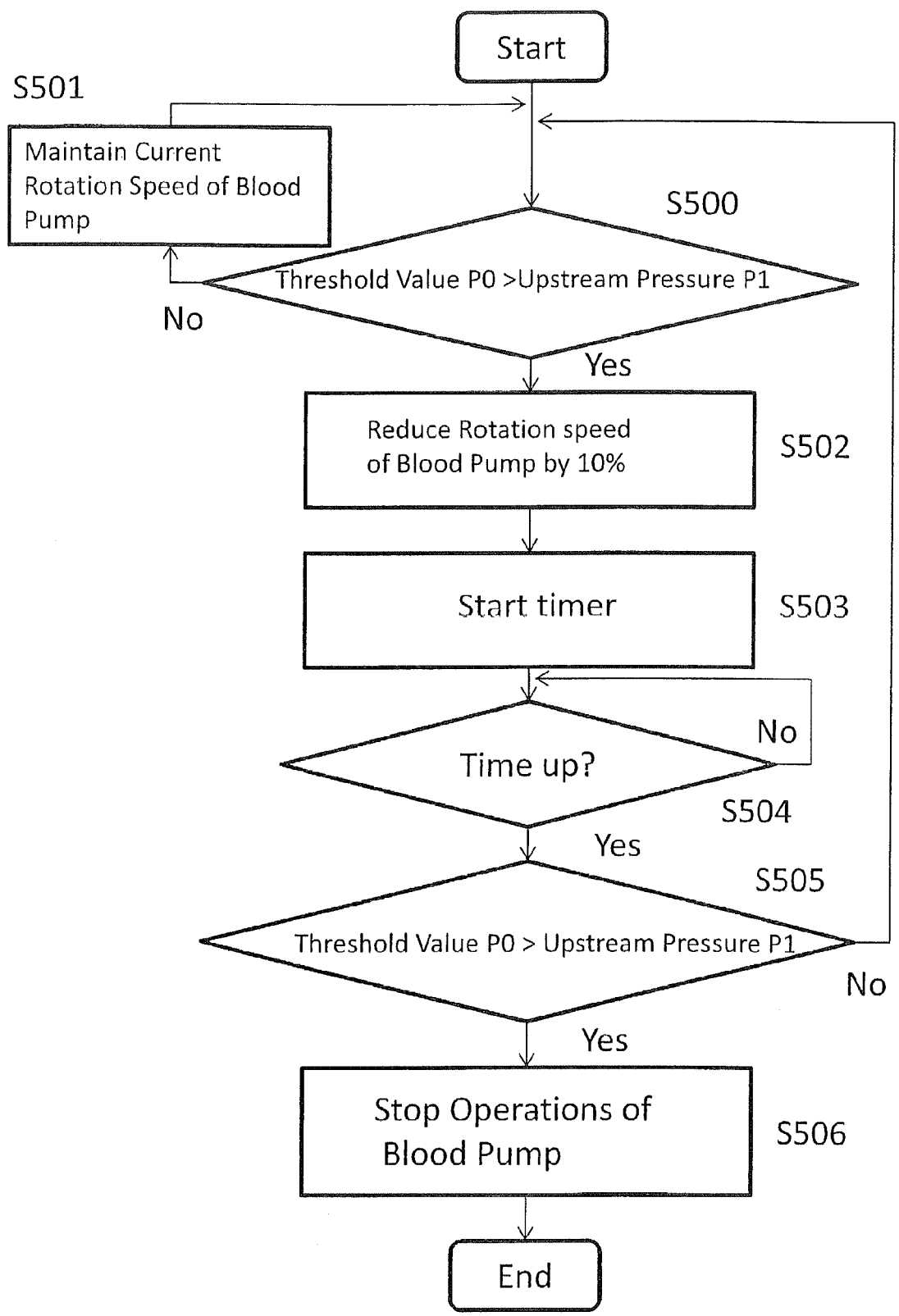
FIG. 13 is a flowchart of a control program executed by a control device for the extracorporeal circuit illustrated in FIG. 12.

FIG. 12 is a schematic illustration of a second embodiment of an extracorporeal circuit representing another example of the extracorporeal circuit disclosed here. FIG. 13 is a flowchart of a control program executed by a control device for the extracorporeal circuit illustrated in FIG. 12, and FIG. 14 represents graphs schematically showing temporal changes in rotation speed of a blood pump under control of the control device for the extracorporeal circuit illustrated in FIG. 12.

This embodiment of the extracorporeal circuit (extracorporeal circulating circuit) 100 can include the oxygenator 1 of the first embodiment or the oxygenator 10 of the second embodiment as described above. In the configuration illustrated in FIG. 12, the extracorporeal circuit 100 includes the oxygenator 10 of the second embodiment. Besides the oxygenator 10, the extracorporeal circuit 100 illustrated in FIG. 12 includes a blood pump 101*d* provided only on the downstream of the oxygenator 10. Further, the extracorporeal circuit 100 has no blood reserving bath provided in conventional extracorporeal circuits, in order to suppress the amount of blood extracorporeally circulating as much as possible.

The oxygenator 10 and a patient's vein (great vein or vena cava) are connected together via a tube 103*f* as a blood removal line. The blood pump 101*d* and the patient's artery are connected together via a tube 103*g* as a blood transmission line. The oxygenator 10 and the blood pump 101*d* are connected together via the tube 103*h* as a relay line. The tube 103*f*, the tube 103*g*, and the tube 103*h* are each flexible.

In the extracorporeal circuit 100, blood is removed from the patient's body by operation of the blood pump 101*d*, and the blood flows downward through the tube 103*f* and flows into the oxygenator 10. In the oxygenator 10, the blood is subjected to gas exchange. Then, the blood having undergone gas exchange flows downward in sequence through the tube 103*h*, the blood pump 101*d*, and the tube 103*g*, and then returns to the heart.

The blood pump 101*d* is a pump configured to transfer blood for extracorporeal circulation. The oxygenator 101*d* may be a centrifugal pump, a roller pump, a bellows pump, or the like. Among the foregoing, the centrifugal pump is preferred because the centrifugal pump is suited for adjustment of the amount of blood extracorporeally circulating and is easy to attach or detach or the like. The amount of blood extracorporeally circulating increases or decreases according to the rotation speed of the centrifugal pump. Specifically, the larger the rotation speed of the centrifugal pump becomes, the more the amount of blood extracorporeally circulating increases. The smaller the rotation speed of the centrifugal pump becomes, the more the amount of blood extracorporeally circulating decreases.

In the thus configured extracorporeal circuit 100, the blood transferring force of the blood pump 101*d* may be excessively large depending on the operating state of the oxygenator 101*d*. In this case, when the rotation speed of the blood pump 101*d* on the downstream of the oxygenator 10 is excessively high due to some abnormality as described above, the pressure in the blood passages 33 may be excessively lower than the internal pressure in the gas passages 32. In this case, gas in the lumens of the hollow fiber membranes 31 may enter into the blood passages 33 and emerge as bubbles. At that time, the bubbles flow through the first filter member 41A at a place of close contact between the hollow fiber membranes 31 and the first filter member 41A. However, the bubbles having flowed through the first filter member 41A are reliably caught by the second filter member 43A and discharged from the discharge port 29. Thus, it is reliably prevented that the bubbles remain mixed in the blood and flow out form the blood outlet port 28, and then are transferred to downstream of the oxygenator 10, that is, a patient's body.

In conventional extracorporeal circuits, in the case where the blood pump is a centrifugal pump, when a large number of bubbles exist in blood, the blood pump comes to run idle and cannot transfer the blood. In the present invention, however, bubbles are removed at the oxygenator 10 to reliably prevent that the functionality of the blood pump 101*d* as a centrifugal pump is deteriorated.

In conventional extracorporeal circuits, an arterial filter is provided in front of a patient (downstream of the extracorporeal circuit) to prevent an inflow of bubbles into a patient's body. In the extracorporeal circuit 100 disclosed here, bubbles are removed at the oxygenator 10, which eliminates the need for an arterial filter. Accordingly, it is possible to suppress the amount of blood extracorporeally circulating by the elimination of an arterial filter and a bubble removal device as described above.

As illustrated in FIG. 12, a pressure sensor 104 is provided upstream of the oxygenator 10, specifically, in an intermediate portion of the tube 103*f*. The pressure sensor is intended to detect a pressure on the upstream side of the oxygenator 10 (tube 103*f*), and may be a diaphragm gauge, for example. The diaphragm gauge is configured to detect a pressure applied to a diaphragm as deformation of the diaphragm.

On the upstream side of the gas inlet port 26 of the oxygenator 10, a valve mechanism 106 is connected in an intermediate portion of a gas line 105 connected to the gas inlet port 26. The valve mechanism 106 is configured to open or close the gas line 105. The valve mechanism 106 may be an electromagnetic valve, for example. The electromagnetic valve is capable of moving an iron piece by a plunger using a magnetic force of an electric magnet, and this movement makes it possible to adjust the amount of gas flowing through the gas line 105. The valve mechanism 106 is generally in an open state and enters into a closed state as necessary to stop the flow of gas.

As described above, the blood transferring force of the blood pump 101*d* may be excessively large depending on the operating state of the blood pump 101*d*. In this case, in the oxygenator 10, the pressure on the blood passage side becomes excessively lower than the pressure on the gas passage side, and thus generated bubbles may flow through the first filter member 41A.

In such a case, however, when the valve mechanism 106 enters into a closed state, it is possible to block off an inflow of gas into the hollow fiber membranes 31 to lower the internal pressure therein. This makes it possible to eliminate the situation in which the pressure on the blood passage side is lower than the pressure on the gas passage side, and prevent reliably the phenomenon that bubbles from the gas passage side emerge on the blood passage side. Accordingly, in synergy with the operation of the second filter member 43A, it is possible to prevent more reliably that bubbles flow out together with blood from the blood outlet port 28 and are transferred to the downstream of the oxygenator 10.

The extracorporeal circuit 100 is provided with a control unit (control means) 107. The control unit 107 is a personal computer containing a CPU (central processing unit), for example, and functions to control operations of the blood pump 101*d*, the pressure sensor 104, and the valve mechanism 106.

A control program executed by the control unit 107 in the extracorporeal circuit 100 will be described below with reference to the flowchart illustrated in FIG. 13. The control program is effective in preventing a situation in which the pressure on the blood passage side is further reduced lower than that described above, and even bubbles caught by the second filter member 43A are sucked in the downstream direction and flow through the second filter member 43A.

The pressure sensor 104 detects pressure $p_1$ in the upstream-side blood passages of the oxygenator 10. Since the tube 103f and the tube 103h communicate with each other via the oxygenator 10, the pressure $p_1$ is the same as the pressure on the downstream of the first filter member 41A. In addition, the operations of the blood pump 101d are controlled according to the pressure $p_1$ (information) detected (obtained) by the pressure sensor 104.

As illustrated in FIG. 13, the control unit 107 stores threshold value $p_0$ in advance. With reference to the threshold value $p_0$, when the pressure $p_1$ is higher than the threshold value $p_0$, even if bubbles have flowed through the first filter member 41A, the bubbles having flowed can be reliably caught by the second filter member 43A. Meanwhile, when the pressure $p_1$ is less than the threshold value $p_0$, the pressure on the downstream of the first filter member 41A becomes excessively lower than the internal pressure in the hollow fiber membranes 31 (than described above), and bubbles may flow through the second filter member 43A. However, the control program makes it possible to prevent that bubbles flow through the second filter member 43A.

As illustrated in FIG. 13, when extracorporeal circulation is started, it is determined whether the pressure $p_1$ detected by the pressure sensor 104 has fallen below the threshold value $p_0$ (step S500). When it is determined that the pressure $p_1$ is equal to or more than the threshold value $p_0$, the then (current) rotation speed of the blood pump 101d is maintained (step S501).

After execution of step S501, the process returns to step S500 to execute the subsequent steps in sequence.

When it is determined at step S500 that the pressure $p_1$ has fallen below the threshold value $p_0$, the rotation speed of the blood pump 101d at that time is decreased by the preset degree of decrease (lowering rate) (10% in this embodiment) (step S502).

Next, a timer contained in the control unit 107 is activated (step S503). When it is determined that a predetermined period of time set in the timer has elapsed (step S504), it is determined again whether the pressure $p_1$ is below the threshold value $p_0$ (step S505).

At step S505, when it is determined that the pressure $p_1$ is equal to or more than the threshold value $p_0$, the process returns to step S500 to execute the subsequent steps in sequence.

When it is determined at step S505 that the pressure $p_1$ is below the threshold value $p_0$, the operations of the blood pump 101d are stopped (step S506).

Under the foregoing control, in the extracorporeal circuit 100, even when bubbles are about to flow through the second filter member 43A, the rotation speed of the blood pump 101d is decreased to prevent a drop in pressure on the blood passage side. This makes it possible to prevent flow of the bubbles in a reliable manner. Accordingly, it is possible to relatively reliably prevent that bubbles in the blood flow out from the oxygenator 10.

In the extracorporeal circuit 100, it is possible to relatively reliably prevent an outflow of bubbles to downstream of the oxygenator 10, which eliminates the need of providing a bubble removal device for removal of bubbles. In addition, it is possible to prevent an outflow of bubbles from the oxygenator 10 to downstream, and thus even when the blood pump 101d provided on the downstream is a centrifugal pump, which makes it possible to relatively reliably prevent deterioration of the pump in functionality. Further, it is possible to make the extracorporeal circuit 100 smaller in size by eliminating the bubble removal device and decrease the amount of blood extracorporeally circulating as much as possible.

Figure 14A:
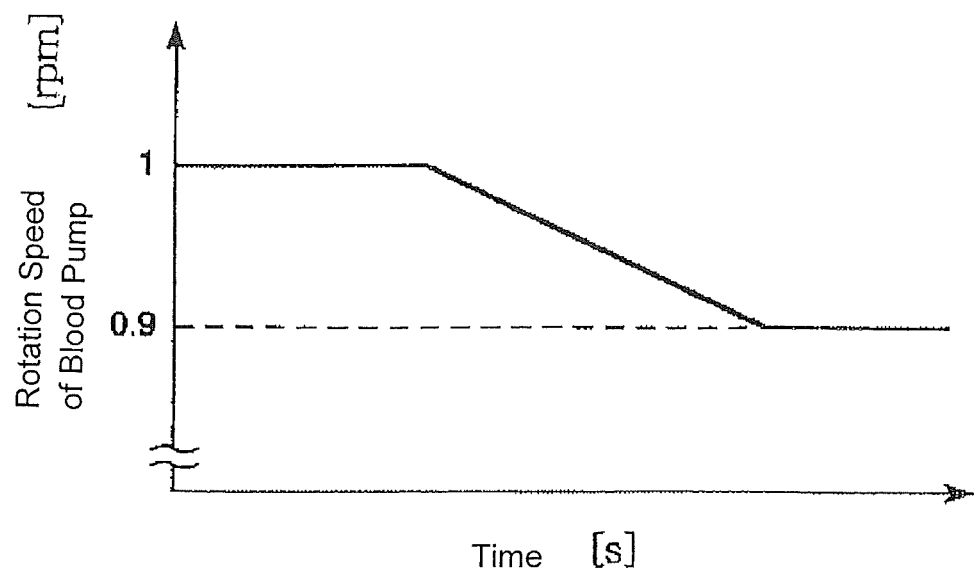
FIGS. 14(*a*) and 14(*b*) represent graphs schematically showing temporal changes in rotation speed of a blood pump under control of the control device for the extracorporeal circuit illustrated in FIG. 12.
Figure 14B:
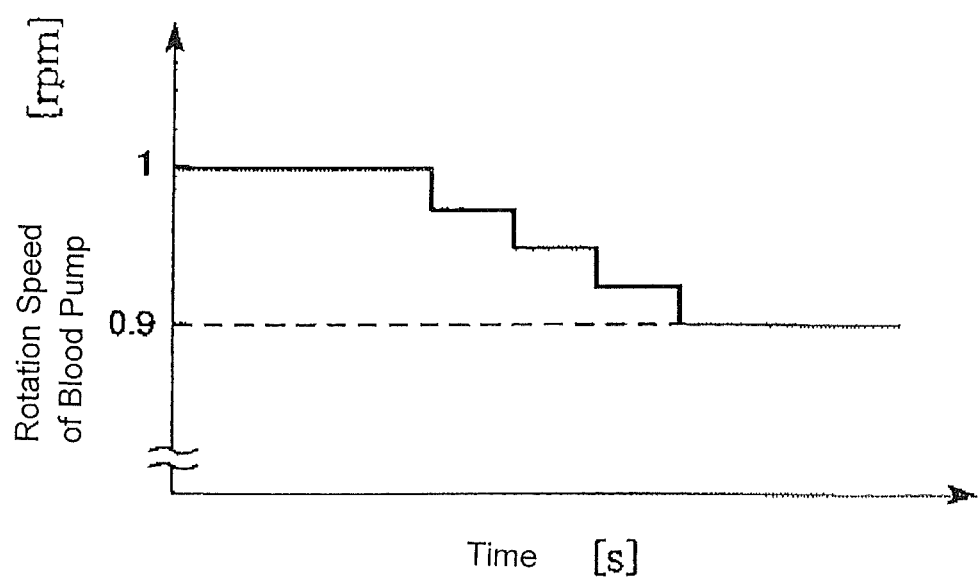

At step S502, the rotation speed of the blood pump 101d is decreased. The decrease may be continuous as illustrated in FIG. 14(a), or may be stepwise as illustrated in FIG. 14(b). When the rotation speed is controlled to be continuously decreased, the rotation speed can be preferably decreased in a quick manner. When the rotation speed is controlled to be decreased stepwise, it is possible to prevent preferably that the rotation speed of the blood pump 101d is excessively decreased.

At step S502, the lowering ratio of the rotation speed of the blood pump 101d is not limited to 10%. For example, the lowering ratio may be preferably a predetermined lowering ratio within the range of 5 to 80%, more preferably a predetermined lowering ratio within the range of 10 to 50%.

The blood pump is provided only downstream of the oxygenator, and only a single blood pump is provided in the configuration illustrated in FIG. 12. However, the number of blood pumps is not limited to one, but may be two or more, for example.

The description above describes embodiments of the oxygenator and the extracorporeal circuit representing examples of the oxygenator and the extracorporeal circuit disclosed here. However, the present invention is not limited to those specific embodiments. For example, components of the oxygenator and the extracorporeal circuit can be replaced with other components capable of exerting similar functions. Alternatively, other components may be added. For example, the structures and shapes of the housing and the heat exchanger, and the formation positions and protrusion directions of the gas inlet port, gas outlet port, blood outlet port, blood inlet port, heat medium inlet port, and heat medium outlet portion, and the like, may be different from those of the illustrated configurations. In addition, the posture of the oxygenator during use (vertical position relationships between the components) is not limited to the illustrated state.

The oxygenator and the extracorporeal circuit may be a combination of two or more arbitrary configurations (features) in the foregoing embodiments.

In the oxygenator of the foregoing embodiments, the discharge port discharging bubbles protrudes from the housing. However, the oxygenator is not limited to this configuration, but may have at an opening formed by penetrating the wall portion of the housing, a hydrophobic filter through which gas flows but liquid (blood) does not flow, for example. Bubbles can be discharged via the filter.

The second filter in the oxygenator of the second embodiment is curved in the configuration illustrated in FIG. 9. However, the second filter is not limited to this, but may be linear-shaped in a view of FIG. 9, for example.

In addition, the oxygenator of the second embodiment allows blood to flow through from inside to outside. However, the oxygenator is not limited to this configuration as it may be configured to allow blood to flow through from outside to inside. In this case, the first filter member is arranged in contact with the inner peripheral portion of the cylindrical hollow fiber membrane bundle, and the second filter member is arranged on the downstream of the first filter member.

The oxygenator disclosed here includes: a housing; a hollow fiber membrane bundle that is stored in the housing and has multiple integrated hollow fiber membranes with a gas exchange function; a gas inlet portion and a gas outlet portion that are provided on the upstream and downstream of gas passages in lumens of the hollow fiber membranes, respectively; a blood inlet portion and a blood outlet portion that are provided on the upstream and downstream of blood passages outside the hollow fiber membranes, respectively; a first filter member that is provided on the hollow fiber membrane bundle in contact with a blood outlet portion side surface so as to cover substantially the entire surface and has a function to catch bubbles in blood; and a second filter member that is separated from the first filter member, positioned between the first filter member and the blood outlet portion, and has a function to catch bubbles in blood.

Accordingly, it is possible to incorporate an oxygenator having two bubble removal filters (the first filter member and the second filter member) into an extracorporeal circuit, which eliminates the need for a conventionally used bubble removal device, for example. This makes it possible to suppress the amount of blood extracorporeally circulating and pursue minimum invasive treatment while providing safety.

The detailed description above describes features and aspects of embodiments of an oxygenator and the extracorporeal circuit disclosed by way of example. The disclosure is not limited, however, to the precise embodiments and variations described. Various changes, modifications and equivalents could be effected by one skilled in the art without departing from the spirit and scope of the disclosure as defined in the appended claims. It is expressly intended that all such changes, modifications and equivalents which fall within the scope of the claims are embraced by the claims.

What is claimed is:

1. An oxygenator comprising:
    a housing;
    a hollow fiber membrane bundle stored in the housing and comprised of multiple integrated hollow fiber membranes to perform gas exchange with blood, the hollow fiber membranes each possessing a lumen constituting a gas passage for the gas;
    a gas inlet portion upstream of the gas passages of the hollow fiber membranes;
    a gas outlet portion downstream of the gas passages of the hollow fiber membranes;
    a blood inlet portion upstream of blood passages outside the hollow fiber membranes;
    a blood outlet portion downstream of blood passages outside the hollow fiber membranes;
    a bubble discharge portion downstream of the gas passages of the hollow fiber membranes;
    a first filter member which filters out bubbles in the blood, the first filter member being provided on the hollow fiber membrane bundle in contact with a blood outlet portion side surface of the hollow fiber membrane bundle to cover substantially the entire blood outlet portion side surface of the hollow fiber membrane bundle; and
    a second filter member which filters out bubbles in the blood, the second filter member being separated from the first filter member, and positioned between the first filter member and the blood outlet portion;
    wherein a gap is formed between the first filter member and the housing, the bubble discharge portion communicating with the gap;
    wherein bubbles filtered out by the first filter member are discharged to outside of the housing through the gas outlet portion;
    wherein bubbles passing through the first filter member are discharged to outside of the housing through the bubble discharge portion; and
    wherein bubbles filtered out by the second filter member are discharged to outside of the housing through the bubble discharge portion.

2. The oxygenator according to claim 1, wherein the first filter member and the second filter member are each in a shape of a sheet.

3. The oxygenator according to claim 2, wherein the second filter member is smaller in area than the first filter member.

4. The oxygenator according to claim 1, wherein the housing is cylinder-shaped, and the first filter member and the second filter member overlap each other in a side view.

5. The oxygenator according to claim 1, wherein the blood outlet portion has a tubular blood outlet port protruding from the housing, and the second filter member is positioned near an end portion of the blood outlet on the housing side.

6. An extracorporeal circuit comprising:
    an oxygenator according to claim 1;
    a first blood pump upstream of the oxygenator and configured to transfer blood for extracorporeal circulation; and
    at least one second blood pump downstream of the oxygenator and configured to transfer blood for extracorporeal circulation.

7. An extracorporeal circuit comprising:
    the oxygenator according to claim 1; and
    a blood pump only downstream of the oxygenator so that no blood pump exists upstream of the oxygenator, the blood pump being configured to transfer blood for extracorporeal circulation.

8. The extracorporeal circuit according to claim 7, further comprising a sensor upstream of the oxygenator to detect a pressure on the upstream.

9. The extracorporeal circuit according to claim 8, further comprising control means configured to control operations of the blood pump and the sensor, wherein the control means controls operations of the blood pump according to information obtained from the sensor.

10. The extracorporeal circuit according to claim 9, wherein the control means controls the operations of the blood pump to decrease an amount of the blood flowing into the oxygenator whenever the pressure detected by the sensor falls below a predetermined threshold.

11. An oxygenator comprising:
    a housing possessing an inner surface;
    a hollow fiber membrane bundle located in the housing and comprised of multiple integrated hollow fiber membranes to perform gas exchange with blood, the hollow fiber membranes each possessing a lumen constituting a gas passage for the gas, the hollow fiber membranes being positioned so that blood passage spaces exist between adjacent hollow fiber membranes through which the blood flows, the hollow fiber membrane bundle possessing a downstream facing outer surface facing downstream relative to a direction of flow of the blood;
    a gas inlet upstream of the gas passages in the hollow fiber membranes, the gas inlet fluidly communicating with the gas passages in the hollow fiber membranes so that gas in the gas inlet flows into the gas passages;
    a gas outlet downstream of the gas passages in the hollow fiber membranes, the gas outlet fluidly communicating with the gas passages in the hollow fiber membranes so that gas in the gas passages flow outside the housing by way of the gas outlet;

a blood inlet upstream of the blood passage spaces, the blood inlet communicating with the blood passage spaces so that blood in the blood inlet flows into the blood passage spaces;

a blood outlet downstream of the blood passage spaces, the blood outlet communicating with the blood passage spaces so that blood in the blood passage spaces flows into the blood outlet;

a bubble discharge portion downstream of the gas passages of the hollow fiber membranes;

a first filter member which filters out bubbles in the blood that has passed through the blood passage spaces, the first filter member possessing an upstream facing outer surface which faces and directly contacts the downstream facing outer surface of the hollow fiber membrane bundle to cover substantially an entirety of the downstream facing outer surface of the hollow fiber membrane bundle; and a second filter member spaced downstream from the first filter member so that a space exists between the first and second filter members, the second filter member filtering out bubbles in the blood which has passed through the first filter member, the second filter member extending across the blood outlet so that the blood passes through the second filter member before flowing completely through the blood outlet;

wherein a gap is formed between the first filter member and the housing, the bubble discharge portion communicating with the gap;

wherein bubbles filtered out by the first filter member are discharged to outside of the housing through the gas outlet;

wherein bubbles passing through the first filter member are discharged to outside of the housing through the bubble discharge portion; and wherein bubbles filtered out by the second filter member are discharged to outside of the housing through the bubble discharge portion.

12. The oxygenator according to claim 11, wherein the first filter member and the second filter member are each flat sheet-shaped filters.

13. The oxygenator according to claim 11, wherein the second filter member is smaller in area than the first filter member.

14. The oxygenator according to claim 11, wherein the second filter member is positioned at an entrance to the blood outlet.

15. The oxygenator according to claim 11, wherein the first filter member is cylinder-shaped, and the second filter member is curved.

16. The oxygenator according to claim 11, wherein the first filter member possesses a downstream facing outer surface that is opposite the upstream facing outer surface of the first filter member, the downstream facing outer surface of the first filter member being spaced from the inner surface of the housing so that a gap exists between the downstream facing outer surface of the first filter member and the inner surface of the housing, and the housing including a discharge port communicating with the gap and through which bubbles caught by the second filter member are discharged outside the housing.

17. An extracorporeal circuit comprising:
the oxygenator according to claim 11;
a first blood pump upstream of the oxygenator and configured to transfer blood for extracorporeal circulation; and
at least one second blood pump downstream of the oxygenator and configured to transfer blood for extracorporeal circulation.

18. An extracorporeal circuit comprising:
the oxygenator according to claim 11; and
a blood pump only downstream of the oxygenator so that no blood pump exists upstream of the oxygenator, the blood pump being configured to transfer blood for extracorporeal circulation.

* * * * *